US011857335B1

(12) United States Patent
Tadi et al.

(10) Patent No.: US 11,857,335 B1
(45) Date of Patent: Jan. 2, 2024

(54) SYSTEMS, METHODS, AND APPARATUSES FOR REHABILITATION AND TRAINING

(71) Applicant: MINDMAZE GROUP SA, Lausanne (CH)

(72) Inventors: Tej Tadi, Lausanne (CH); Nicolas Fremaux, Lausanne (CH); Jose Rubio, Lausanne (CH); Jonas Ostlund, Lausanne (CH); Sebastien Lasserre, Lausanne (CH); Léandre Bolomey, Lausanne (CH)

(73) Assignee: MINDMAZE GROUP SA, Lausanne (CH)

( * ) Notice: Subject to any disclaimer, the term of this patent is extended or adjusted under 35 U.S.C. 154(b) by 1005 days.

(21) Appl. No.: 16/170,341

(22) Filed: Oct. 25, 2018

Related U.S. Application Data

(60) Provisional application No. 62/661,182, filed on Apr. 23, 2018, provisional application No. 62/641,026, filed on Mar. 9, 2018, provisional application No. 62/576,777, filed on Oct. 25, 2017.

(51) Int. Cl.
| | |
|---|---|
| *G06V 40/20* | (2022.01) |
| *A61B 5/00* | (2006.01) |
| *G06T 7/246* | (2017.01) |
| *G06T 7/00* | (2017.01) |
| *A61B 5/11* | (2006.01) |
| *A63F 13/213* | (2014.01) |

(52) U.S. Cl.
CPC ............ *A61B 5/486* (2013.01); *A61B 5/1124* (2013.01); *A61B 5/1128* (2013.01); *A61B 5/7246* (2013.01); *A61B 5/7445* (2013.01); *A63F 13/213* (2014.09); *G06T 7/0012* (2013.01); *G06T 7/246* (2017.01); *G06V 40/20* (2022.01); *A61B 5/1127* (2013.01); *A61B 2505/09* (2013.01); *G06T 2207/10028* (2013.01); *G06T 2207/30196* (2013.01); *G06T 2207/30204* (2013.01)

(58) Field of Classification Search
CPC . A61B 2505/09; A61B 5/7445; A61B 5/7246; A61B 5/1128; A61B 5/1124; A61B 5/486; G06V 40/20; G06T 7/0012; A63F 13/213
USPC ........................................................ 434/258
See application file for complete search history.

(56) References Cited

U.S. PATENT DOCUMENTS

| | | | |
|---|---|---|---|
| 2013/0162674 A1* | 6/2013 | Nakamura | G06V 20/20 345/633 |
| 2017/0258390 A1* | 9/2017 | Howard | A61B 5/369 |
| 2018/0121728 A1* | 5/2018 | Wells | A61B 5/015 |
| 2020/0085668 A1* | 3/2020 | Yu | A63B 21/00181 |

* cited by examiner

*Primary Examiner* — Gordon G Liu
(74) *Attorney, Agent, or Firm* — GRAESER ASSOCIATES INTERNATIONAL INC.; D'Vorah Graeser

(57) ABSTRACT

Systems, methods and apparatuses for rehabilitation and/or training of a subject. Rehabilitation may be performed after neurological damage has occurred, including without limitation acute or chronic damage. Training as referred to herein relates to any process performed in order to improve the physical and/or cognitive function of a subject.

17 Claims, 34 Drawing Sheets

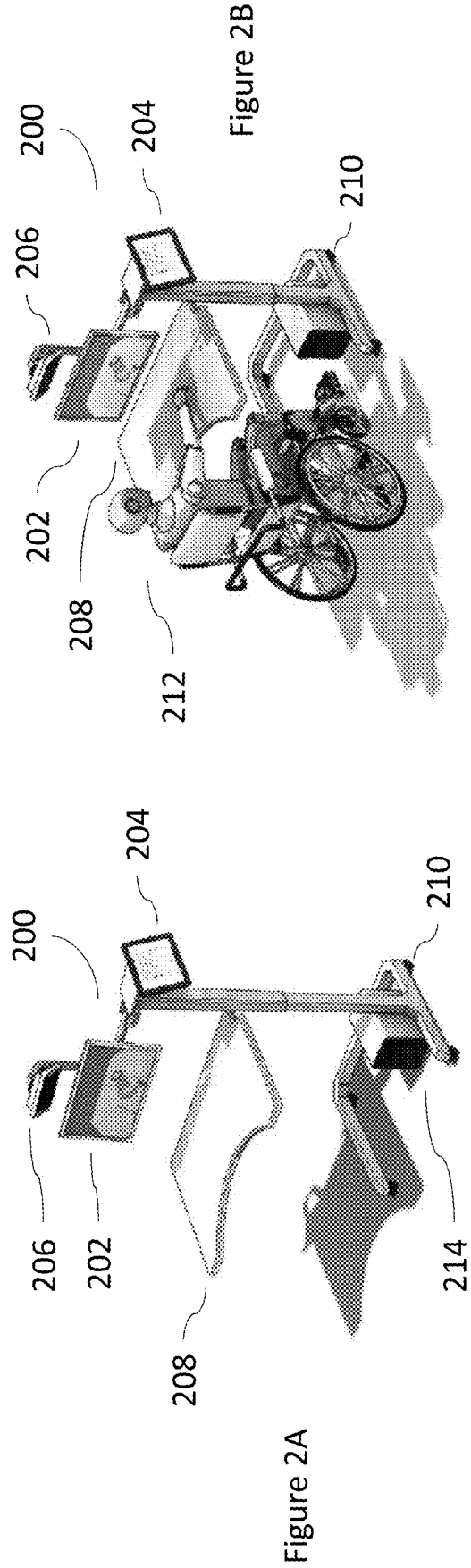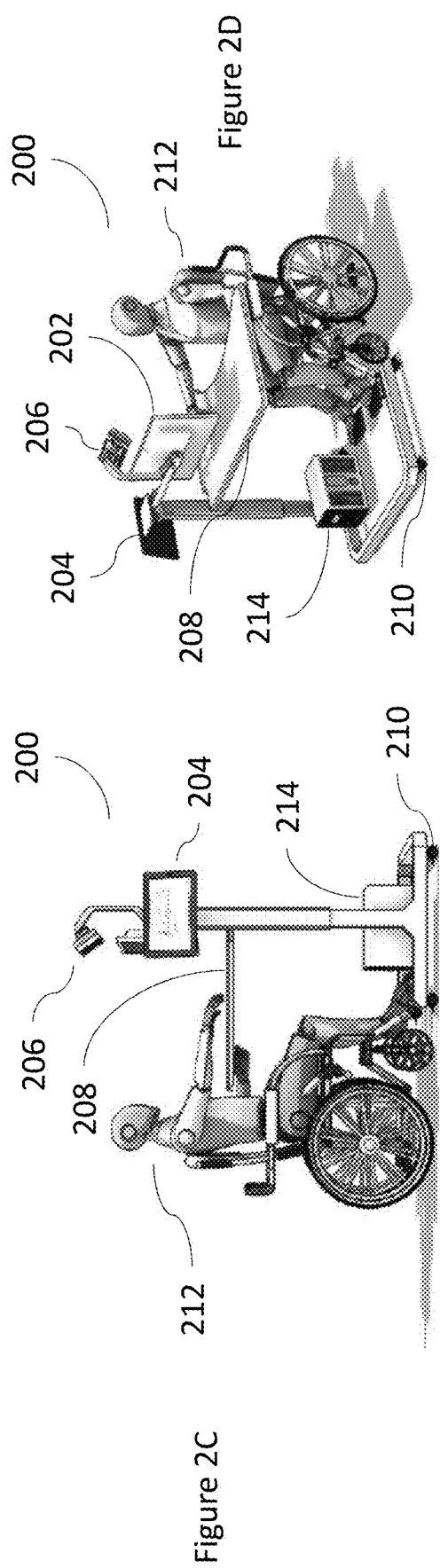
Figure 2A
Figure 2B
Figure 2C
Figure 2D

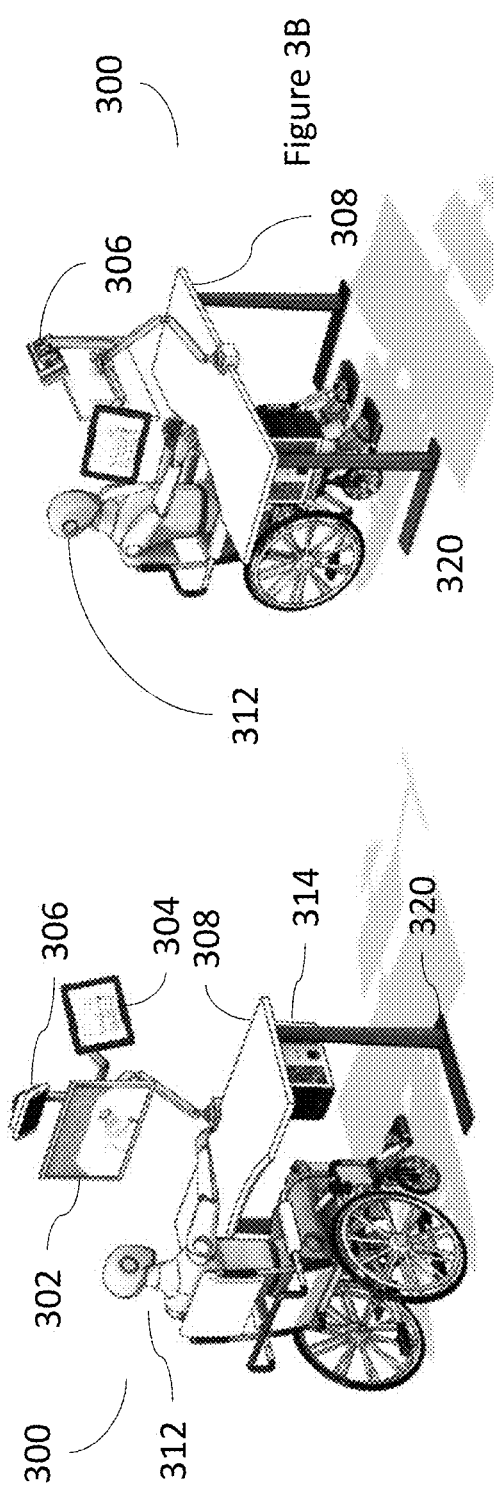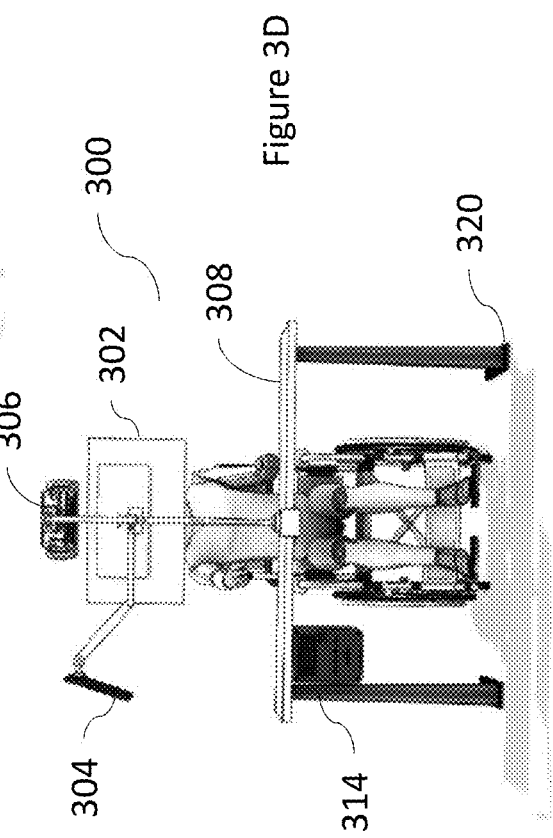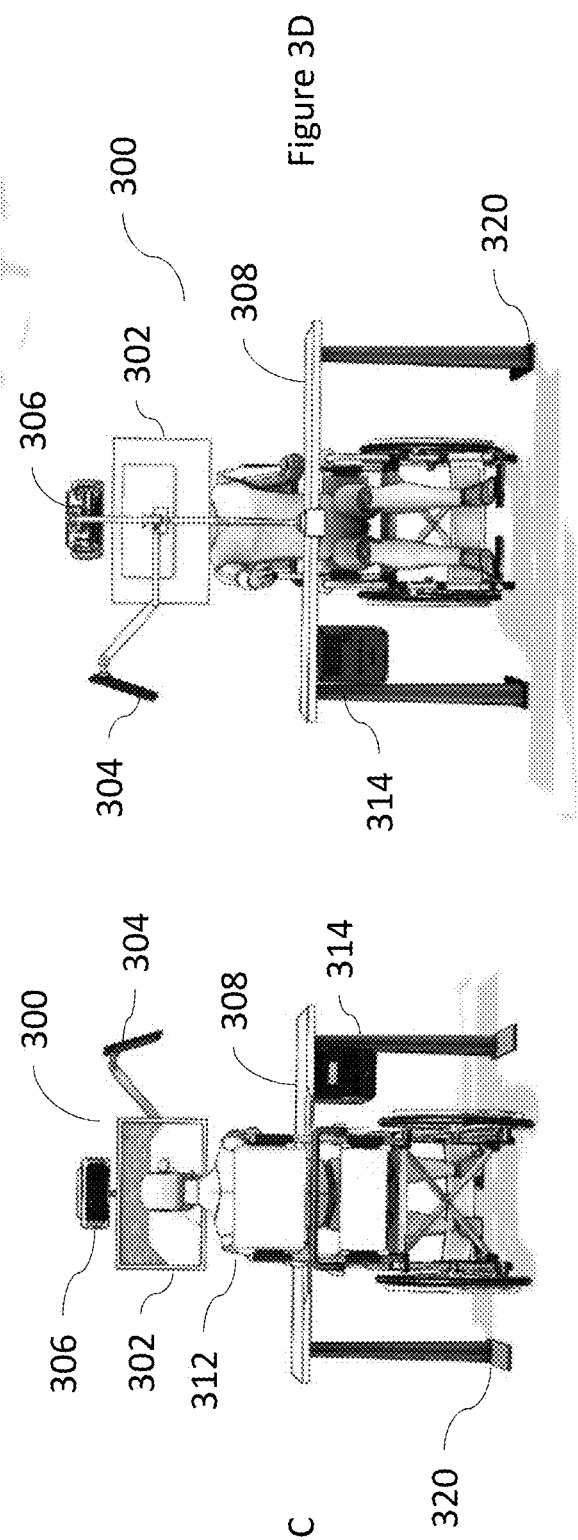

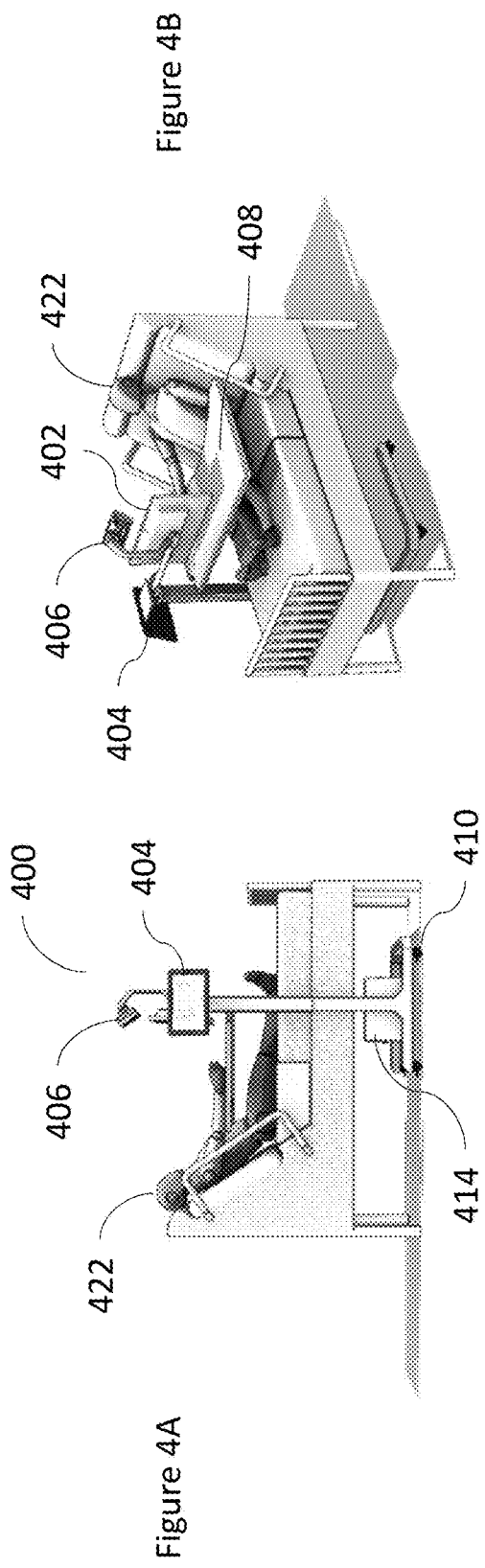
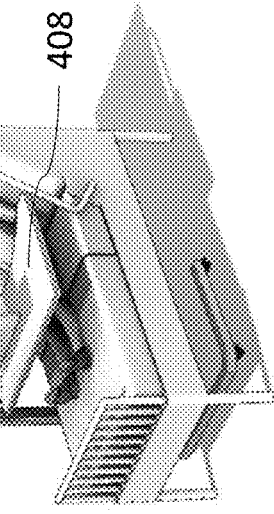
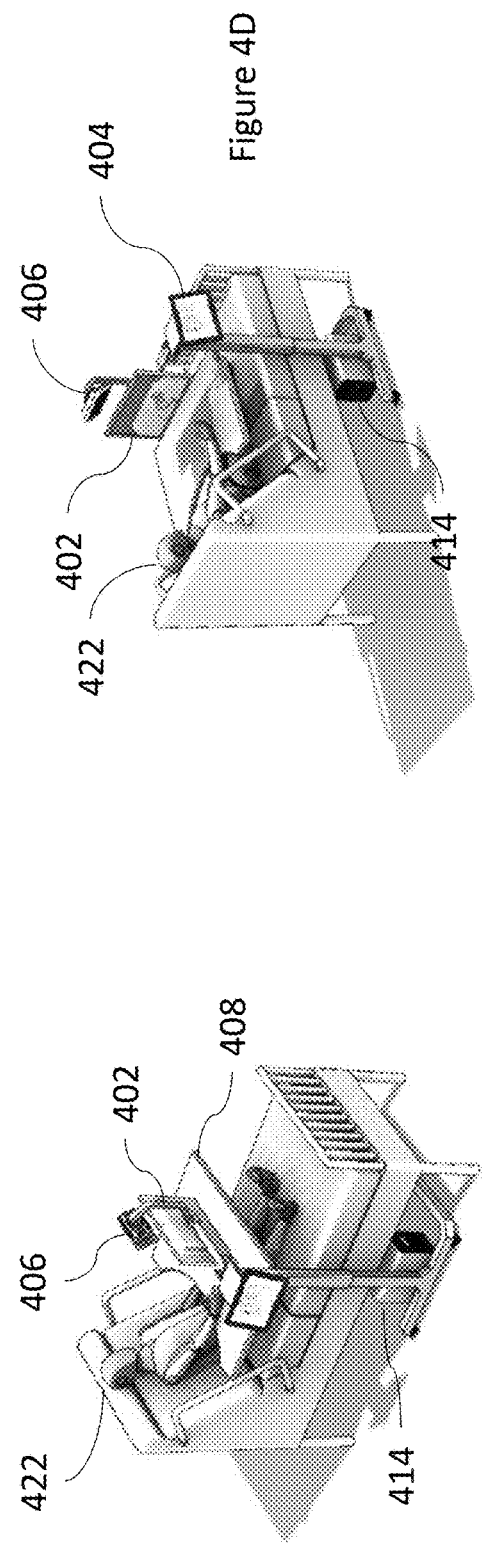
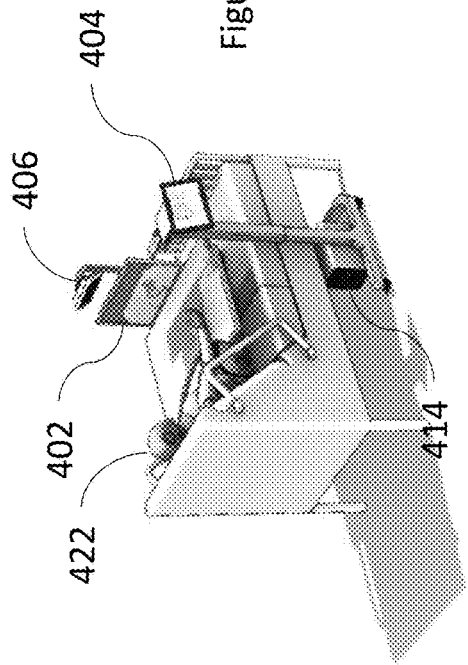

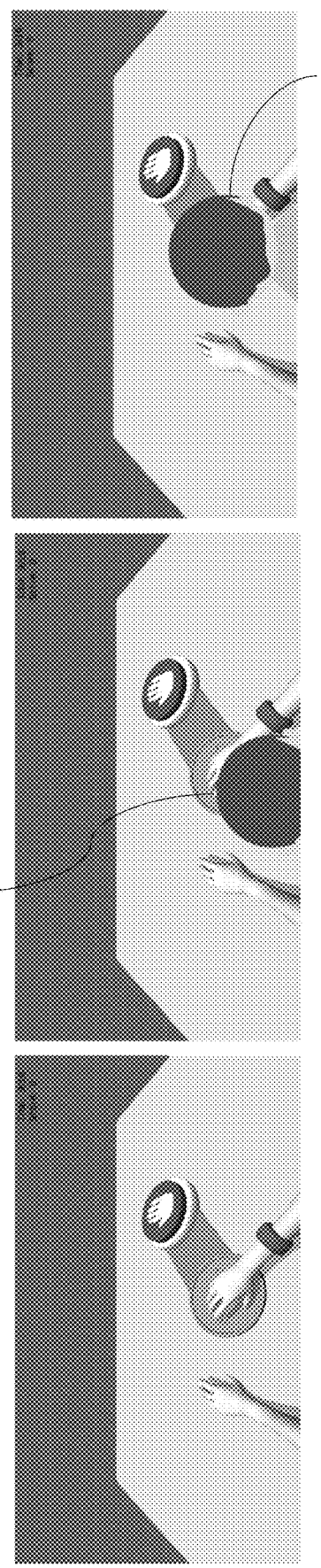

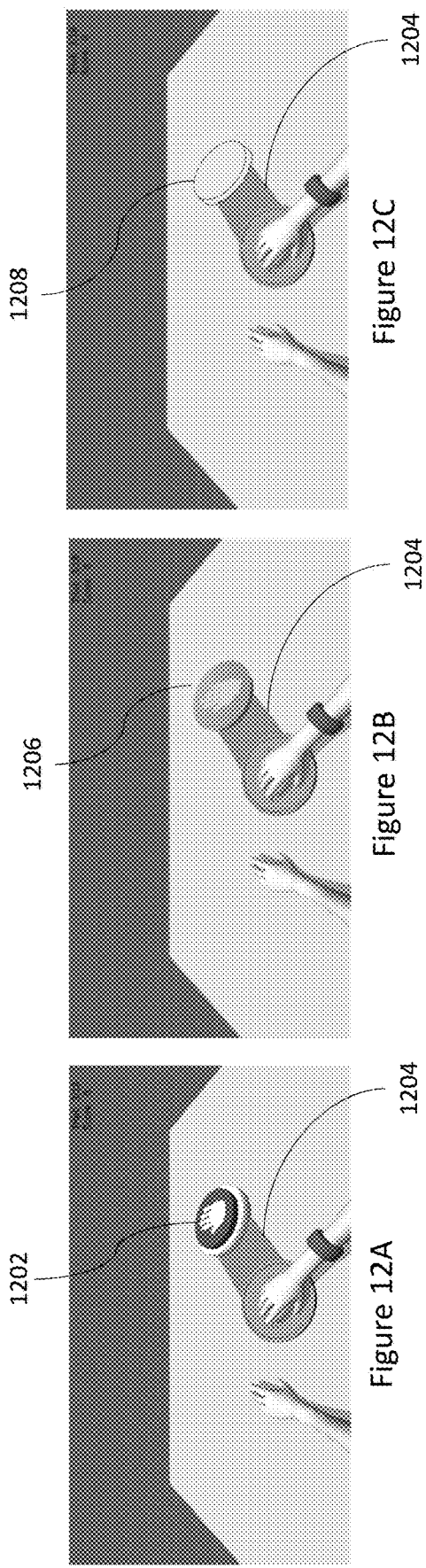

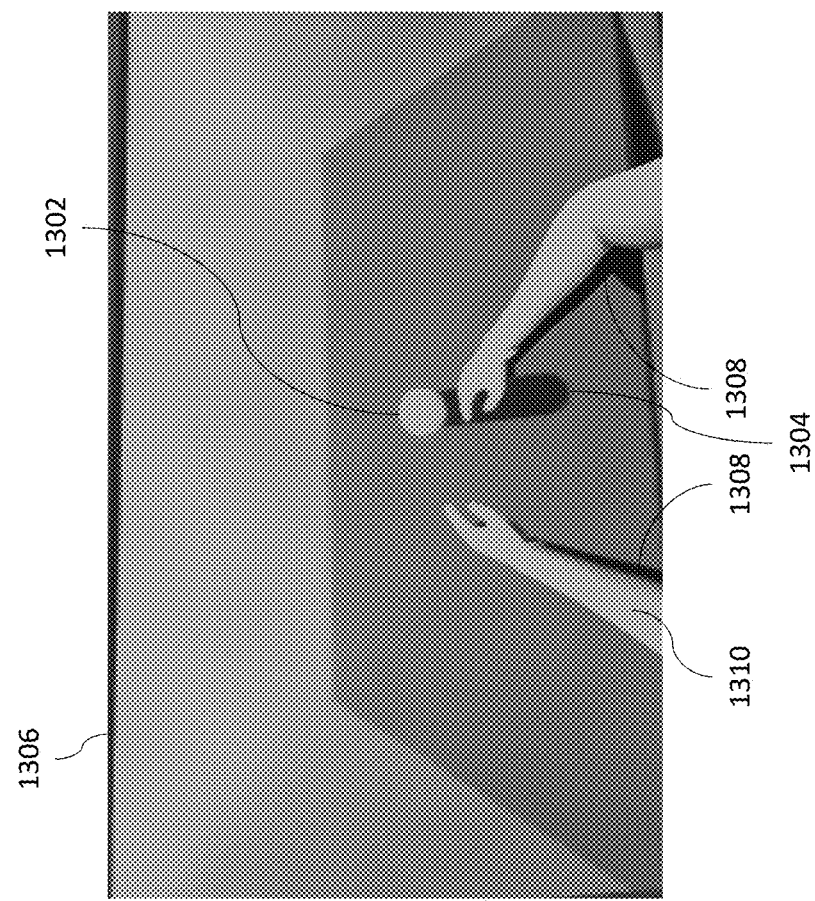
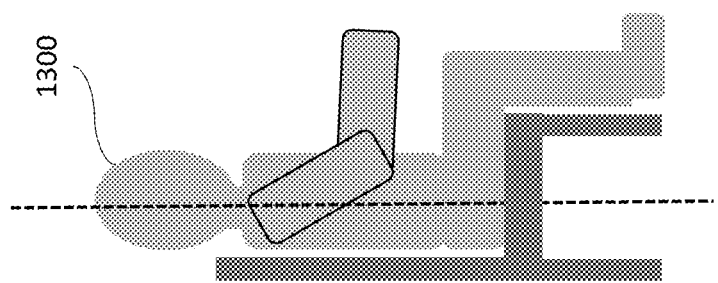
Figure 13A

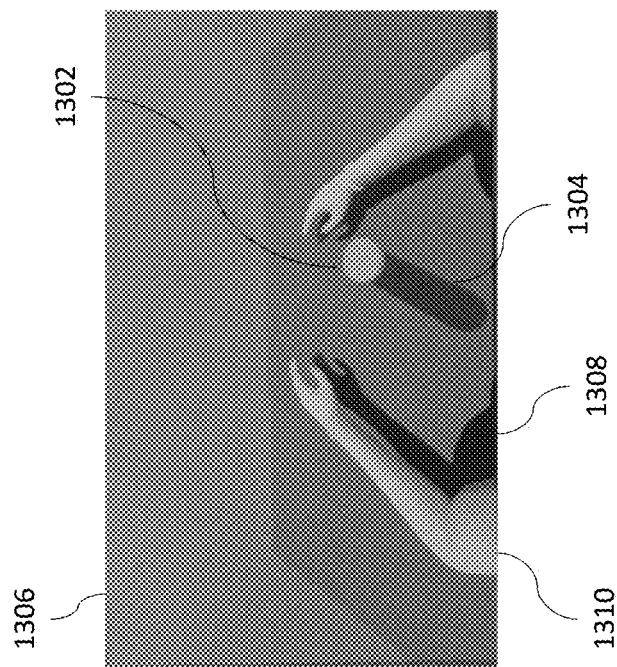
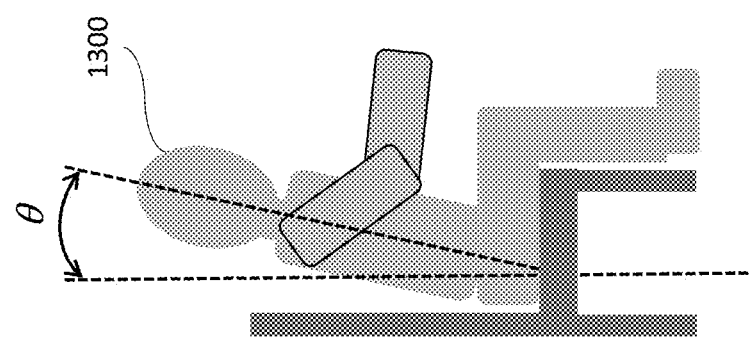
Figure 13B

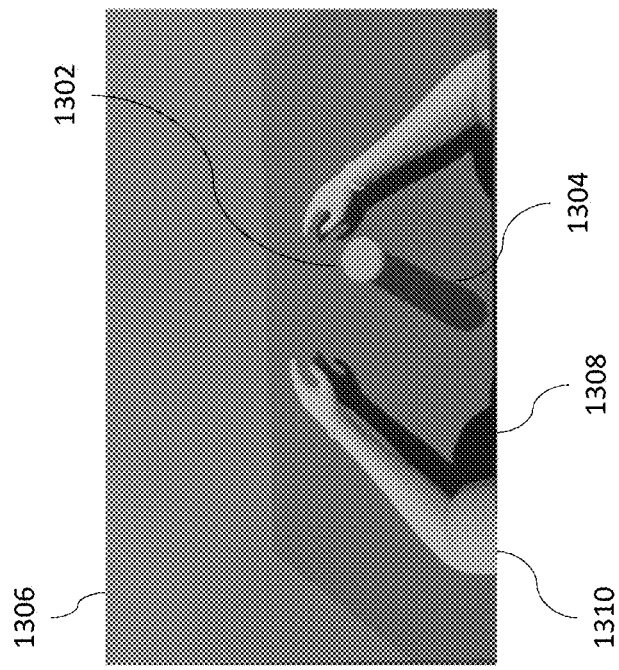
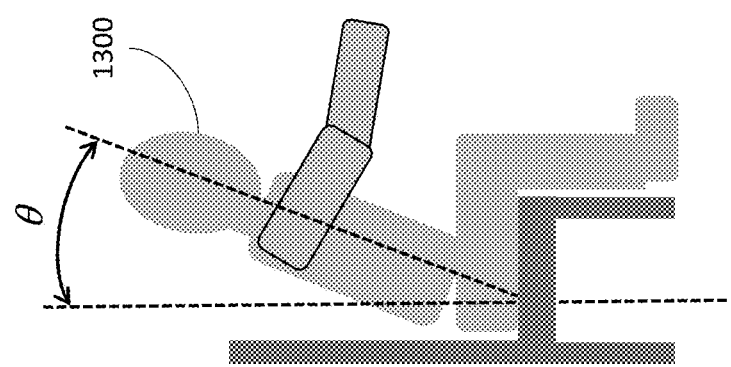
Figure 13C

| Class | Format | Description |
|---|---|---|
| BioSig | [...] | - min |
| | PHYSICAL_D | - max |
| | DIGITAL_I24 | - ch. info |
| IMU | [...] | - active fields |
| | IMU_D | - num sensors |
| | IMU_F | |
| Range | [...] | - resolution |
| | PC_F128 | - stride |
| | DEPTH_F | - PC flag |
| | PHASES16 | |
| Image | [...] | - resolution |
| | MONO16 | - stride |
| | BAYER_BGGR8 | |
| | RGBA32 | |
| | BGR24 | |

1804 / 1806 / 1808

1802 Capability

Full description

SYSTEMS, METHODS, AND APPARATUSES FOR REHABILITATION AND TRAINING

FIELD OF THE DISCLOSURE

The present invention is of a system, method and apparatus for software for rehabilitation and training, and in particular, to such a system, method and apparatus that features software for performing such rehabilitation and/or training with a depth sensor and/or camera.

BACKGROUND OF THE DISCLOSURE

A stroke is a cerebrovascular accident that happens when the blood flow to a portion of the brain is disrupted, resulting in brain cell death. The consequences can be physical as well as cognitive, and can lead to a decrease in movement function and a loss of independence. This disorder is a major cause of long-term physical disabilities and handicaps in Western countries, mostly in the older age range of the population. Thus, as the worldwide population is aging, this disorder is one of the main concern for the future of health care due to budgetary constraints limiting the intensity and length of the conventional rehabilitative treatment consisting of physical and occupational therapy (C. Bosecker et al. Kinematic robot-based evaluation scales and clinical counterparts to measure upper limb motor performance in patients with chronic stroke. Neurorehabilitation and Neural Repair, 2010).

In order to overcome the effects of a stroke, rehabilitation or "rehab" is necessary. This process includes physical exercises overseen by a therapist, to return as much function to the user as possible. However, human therapists are limited and expensive. Aging populations will continue to demand more healthcare at ever greater expense, reducing access to human therapists by patients in need of treatment.

Another significant problem is that traditional post-stroke rehabilitation exercises are considered to be very boring by the patients. As part of the Horizon 2020, the European Commission funded a project which showed that gamification increased patient interest in performing the rehabilitation exercises, causing them to work harder, even without realizing it (https://ec.europa.eu/programmes/horizon2020/en/news/video-games-or-exercise-stroke-rehab).

SUMMARY OF AT LEAST THE INVENTION

Embodiments of the present disclosure are directed to systems, methods and apparatuses for rehabilitation and/or training of a subject. Rehabilitation may be performed after neurological damage has occurred, including without limitation acute or chronic damage. Acute damage may for example by caused by a stroke, accident (e.g. a blow to the head, concussion and the like) or by any other acute injury. Chronic damage may result from an acute injury and/or may be caused by a chronic disease process, such as a neurological disease for example.

Preferred embodiments can include:
Workspace definition: in preferred embodiments, the patient workspace displayed in the virtual environment can be adapted based on a reachable area of the patient. The workspace vertices and edges can be customized and the distribution of virtual objects within the workspace can be adjusted.
Parametrization and customization according to patient motor and cognitive skills: Preferred embodiments can include a set of parameters to tailor the activity on patient skills. The set of parameters can be linked with activity levels and integration of cognitive elements.
Compensation feedback: in preferred embodiments, feedback appears when compensation movements are engaged during an activity.
Cognitive load: in preferred embodiments, different levels of cognitive load can be integrated as a parameter of the activities.
Visual load: in preferred embodiments, different levels of visual load are integrated as a parameter of the activities.
Multi-modal feedback (auditory and visual): in preferred embodiments, sound and visual feedback are integrated within the activity. The different feedback can be modulated.
Accurate and robust tracking/embodiment: in preferred embodiments, the avatar mapping module is verified and validated with patients and therapist. Hybrid tracking and hand trackers are used to mitigate perturbations of magnetic field.
Tracking calibration improvement: in preferred embodiments, tracking calibration time and complexity are reduced.
Mirror mapping: in preferred embodiments, mapping upper limb movement on contra-lateral side can be performed.
Training as referred to herein relates to any process performed in order to improve the physical and/or cognitive function of a subject.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the apparatuses, devices, methods and systems of the present disclosure involve performing or completing certain selected tasks or steps manually, automatically, or a combination thereof. Specifically, several selected steps can be implemented by hardware or by software on an operating system, of a firmware, and/or a combination thereof. For example, as hardware, selected steps of at least some embodiments of the disclosure can be implemented as a chip or circuit (e.g., ASIC). As software, selected steps of at least some embodiments of the disclosure can be implemented as a number of software instructions being executed by a computer (e.g., a processor of the computer) using an operating system. In any case, selected steps of methods of at least some embodiments of the disclosure can be described as being performed by a processor, such as a computing platform for executing a plurality of instructions.

Software (e.g., an application, computer instructions) which is configured to perform (or cause to be performed) certain functionality may also be referred to as a "module" for performing that functionality, and also may be referred to a "processor" for performing such functionality. Thus, processor, according to some embodiments, may be a hardware component, or, according to some embodiments, a software component.

Further to this end, in some embodiments: a processor may also be referred to as a module; in some embodiments, a processor may comprise one more modules; in some embodiments, a module may comprise computer instructions—which can be a set of instructions, an application, software—which are operable on a computational device (e.g., a processor) to cause the computational device to conduct and/or achieve one or more specific functionality. Furthermore, the phrase "abstraction layer" or "abstraction interface", as used with some embodiments, can refer to computer instructions (which can be a set of instructions, an application, software) which are operable on a computational device (as noted, e.g., a processor) to cause the computational device to conduct and/or achieve one or more specific functionality. The abstraction layer may also be a circuit (e.g., an ASIC) to conduct and/or achieve one or more specific functionality. Thus, for some embodiments, and claims which correspond to such embodiments, the noted feature/functionality can be described/claimed in a number of ways (e.g., abstraction layer, computational device, processor, module, software, application, computer instructions, and the like).

Some embodiments are described with regard to a "computer", a "computer network," and/or a "computer operational on a computer network," it is noted that any device featuring a processor (which may be referred to as "data processor"; "pre-processor" may also be referred to as "processor") and the ability to execute one or more instructions may be described as a computer, a computational device, and a processor (e.g., see above), including but not limited to a personal computer (PC), a server, a cellular telephone, an IP telephone, a smart phone, a PDA (personal digital assistant), a thin client, a mobile communication device, a smart watch, head mounted display or other wearable that is able to communicate externally, a virtual or cloud based processor, a pager, and/or a similar device. Two or more of such devices in communication with each other may be a "computer network."

BRIEF DESCRIPTION OF THE DRAWINGS

Embodiments of the present disclosure herein described are by way of example only, with reference to the accompanying drawings. With specific reference now to the drawings in detail, it is stressed that the particulars shown are by way of example and for purposes of illustrative discussion of some embodiments of the present invention only, and are presented in order to provide what is believed to be the most useful and readily understood description of the principles and conceptual aspects of some of the embodiments. In this regard, no attempt is made to show details of some embodiments in more detail than is necessary for a fundamental understanding thereof.

FIGS. 2A-2D show an exemplary, illustrative, non-limiting configuration of a mobile, table based system for supporting rehabilitation according to at least some embodiments of the present disclosure;

FIGS. 3A-3D show an exemplary, illustrative, non-limiting configuration of another table based system for supporting rehabilitation according to at least some embodiments of the present disclosure;

FIGS. 4A-4D show an exemplary, illustrative, non-limiting configuration of a system that is suitable for a subject in a bed, for supporting rehabilitation according to at least some embodiments of the present disclosure;

FIGS. 11A-11C, 12A-12C, and 13A-13C illustrate exemplary types of compensatory movement feedback in accordance with embodiments;

FIG. 17A shows an exemplary, non-limiting, illustrative software architecture for a device abstraction layer while

FIG. 18 shows an exemplary, non-limiting, illustrative data type description;

DESCRIPTION OF AT LEAST SOME EMBODIMENTS

Figure 1A:
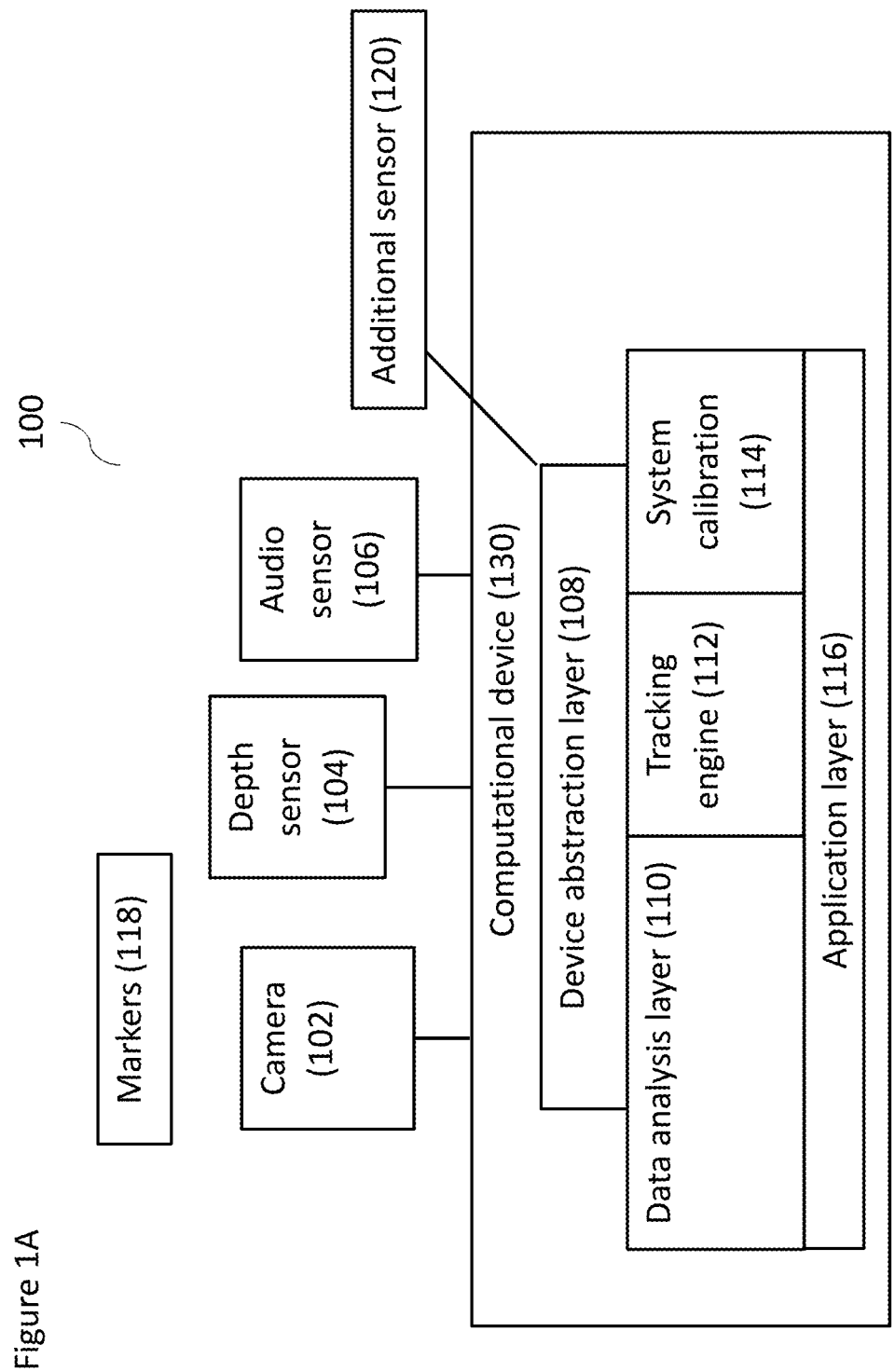
FIGS. 1A, 1B and 1C show a non-limiting example of systems according to at least some embodiments of the present disclosure.
Figure 1B:
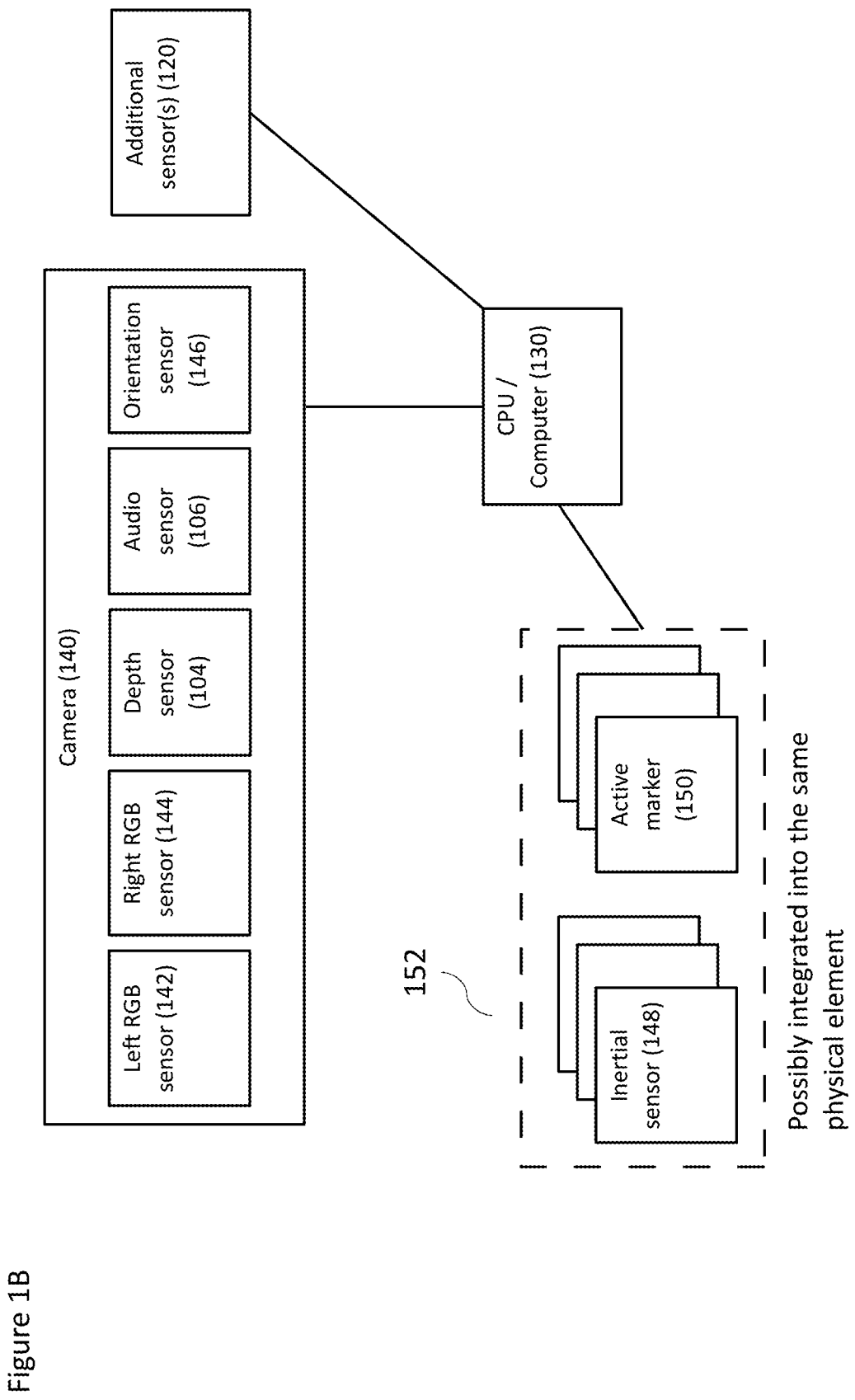

FIG. 1A shows a non-limiting example of a system according to at least some embodiments of the present disclosure. As shown, a system 100 features a camera 102, a depth sensor 104 and optionally an audio sensor 106. Optionally an additional sensor 120 is also included. Optionally camera 102 and depth sensor 104 are combined in a single product (e.g., Kinect® product of Microsoft®, and/or as described in U.S. Pat. No. 8,379,101). FIG. 1B shows an exemplary implementation for camera 102 and depth sensor 104. Optionally, camera 102 and depth sensor 104 can be implemented with the LYRA camera of Mindmaze SA. The integrated product (i.e., camera 102 and depth sensor 104) enables, according to some embodiments, the orientation of camera 102 to be determined with respect to a canonical reference frame. Optionally, three or all four sensors (e.g., a plurality of sensors) are combined in a single product.

The sensor data, in some embodiments, relates to physical actions of a user (not shown), which are accessible to the sensors. For example, camera 102 can collect video data of one or more movements of the user, while depth sensor 104 may provide data to determine the three dimensional location of the user in space according to the distance of the user from depth sensor 104 (or more specifically, the plurality of distances that represent the three dimensional volume of the user in space). Depth sensor 104 can provide TOF (time of flight) data regarding the position of the user, which, when combined with video data from camera 102, allows a three dimensional map of the user in the environment to be determined. As described in greater detail below, such a map enables the physical actions of the user to be accurately determined, for example, with regard to gestures made by the user. Audio sensor 106 preferably collects audio data regarding any sounds made by the user, optionally including, but not limited to, speech. Additional sensor 120 can collect biological signals about the user and/or may collect additional information to assist the depth sensor 104.

Sensor signals are collected by a device abstraction layer 108, which preferably converts the sensor signals into data which is sensor-agnostic. Device abstraction layer 108 preferably handles the necessary preprocessing such that, if different sensors are substituted, only changes to device abstraction layer 108 would be required; the remainder of system 100 can continue functioning without changes (or, in some embodiments, at least without substantive changes). Device abstraction layer 108 preferably also cleans signals, for example, to remove or at least reduce noise as necessary, and can also be used to normalize the signals. Device abstraction layer 108 may be operated by a computational device (not shown), and any method steps may be performed by a computational device (note—modules and interfaces disclosed herein are assumed to incorporate, or to be operated by, a computational device, even if not shown).

The preprocessed signal data from the sensors can then be passed to a data analysis a layer 110, which preferably performs data analysis on the sensor data for consumption by an application layer 116 (according to some embodiments, "application," means any type of interaction with a user). Preferably, such analysis includes tracking analysis, performed by a tracking engine 112, which can track the position of the user's body and also can track the position of one or more body parts of the user, including but not limited, to one or more of arms, legs, hands, feet, head and so forth. Tracking engine 112 can decompose physical actions made by the user into a series of gestures. A "gesture" in this case may include an action taken by a plurality of body parts of the user, such as taking a step while swinging an arm, lifting an arm while bending forward, moving both arms, and so forth. Such decomposition and gesture recognition can also be done separately, for example, by a classifier trained on information provided by tracking engine 112 with regard to tracking the various body parts.

It is noted that while the term "classifier" is used throughout, this term is also intended to encompass "regressor". For machine learning, the difference between the two terms is that for classifiers, the output or target variable takes class labels (that is, is categorical). For regressors, the output variable assumes continuous variables (see, for example, http://scottge.net/2015/06/14/ml101-regression-vs-classification-vs-clustering-problems/).

The tracking of the user's body and/or body parts, optionally decomposed to a series of gestures, can then be provided to application layer 116, which translates the actions of the user into a type of reaction and/or analyzes these actions to determine one or more action parameters. For example, and without limitation, a physical action taken by the user to lift an arm is a gesture which could translate to application layer 116 as lifting a virtual object. Alternatively or additionally, such a physical action could be analyzed by application layer 116 to determine the user's range of motion or ability to perform the action.

To assist in the tracking process, optionally, one or more markers 118 can be placed on the body of the user. Markers 118 optionally feature a characteristic that can be detected by one or more of the sensors, such as by camera 102, depth sensor 104, audio sensor 106 or additional sensor 120. Markers 118 can be detectable by camera 102, for example, as optical markers. While such optical markers may be passive or active, preferably, markers 118 are active optical markers, for example featuring an LED light. More preferably, each of markers 118, or alternatively each pair of markers 118, can comprise an LED light of a specific color which is then placed on a specific location of the body of the user. The different colors of the LED lights, placed at a specific location, convey a significant amount of information to the system through camera 102; as described in greater detail below, such information can be used to make the tracking process efficient and accurate. Additionally, or alternatively, one or more inertial sensors can be added to the hands of the user as a type of marker 118, which can be enabled as Bluetooth or other wireless communication, such that the information would be sent to device abstraction layer 108. The inertial sensors can also be integrated with an optical component in at least markers 118 related to the hands, or even for more such markers 118. The information can then optionally be integrated to the tracking process, for example, to provide an estimate of orientation and location for a particular body part, for example as a prior restraint.

Data analysis layer 110, in some embodiments, includes a system calibration module 114. As described in greater detail below, system calibration module 114 is configured to calibrate the system with respect to the position of the user, in order for the system to track the user effectively. System calibration module 114 can perform calibration of the sensors with respect to the requirements of the operation of application layer 116 (although, in some embodiments—which can include this embodiment—device abstraction layer 108 is configured to perform sensor specific calibration). Optionally, the sensors may be packaged in a device (e.g., Microsoft® Kinect), which performs its own sensor specific calibration.

FIG. 1B shows a non-limiting example of the implementation of the camera and depth sensor, according to at least some embodiments of the present disclosure (components with the same or similar function from earlier figures are labeled with the same component numbers). Here, a camera 140 includes a plurality of different sensors incorporated therein, including, without limitation, a left RGB (red green blue) sensor 142, a right RGB sensor 144, depth sensor 104, audio sensor 106 and an orientation sensor 146. Orientation sensor 146 is configured to provide information on the orientation of the camera.

The markers of FIG. 1A are now shown in more detail, as markers 152. Markers 152 preferably comprise an inertial sensor 148 and an active marker 150. Active marker 150 can comprise any type of marker which issues a detectable signal, including but not limited to an optical signal such as from an LED light as previously described. A plurality of different markers 152 can be provided; active marker 150 can be adjusted for the plurality of markers 152, for example to show LED lights of different colors as previously described.

Figure 1C:
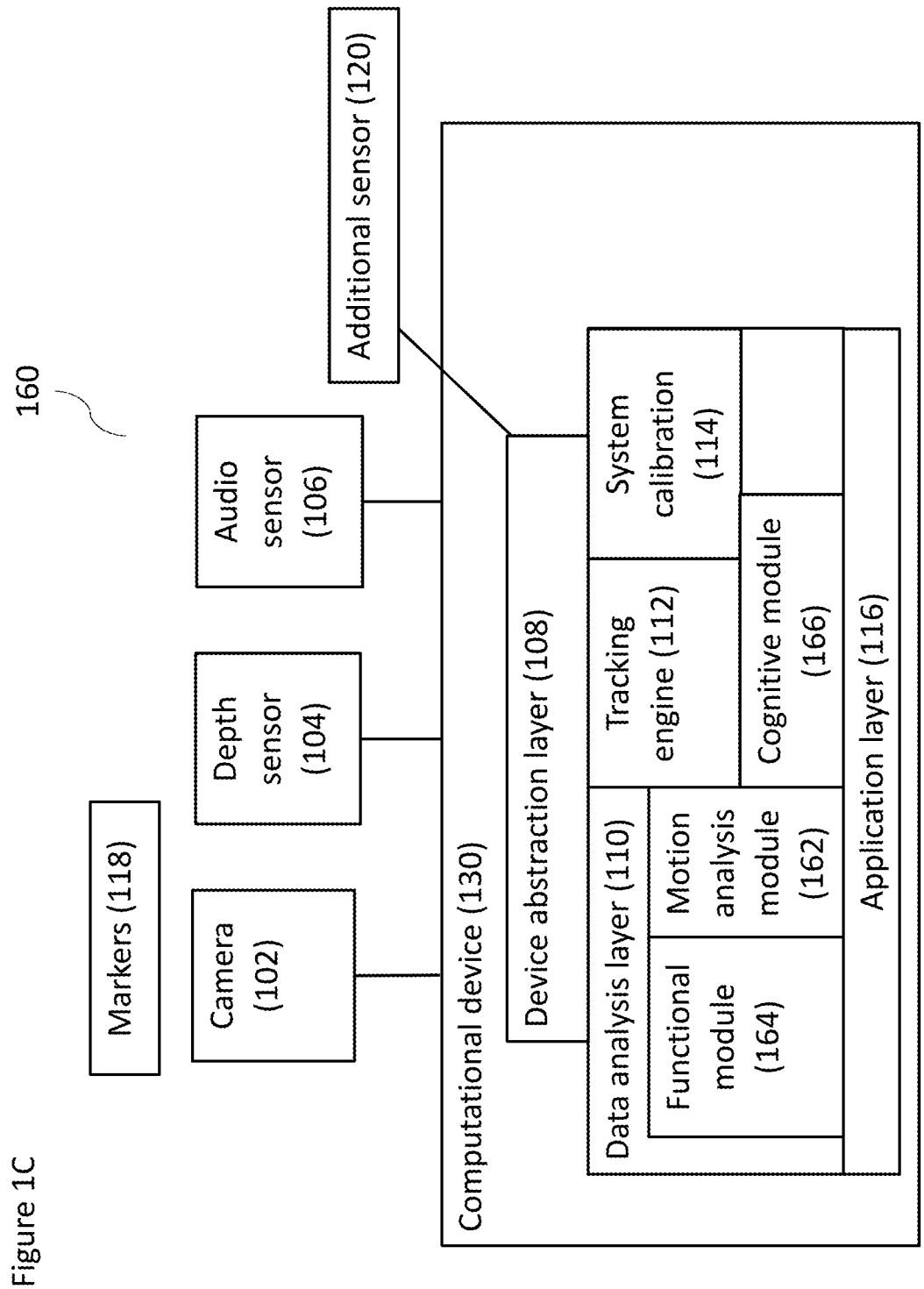

FIG. 1C shows a variation on the above systems, in a non-limiting, illustrative, exemplary system 160. System 160 includes various components as previously described, which have the same reference number as these previously described components, and the same or similar function.

System 160 also includes a motion analysis module 162, a functional assessment module 164 and a cognitive assessment module 166. Motion analysis module 162 is preferably in communication with tracking engine 112, to receive information on tracking of the patient's movements. Motion analysis module 162 optionally and preferably provides feedback on the patient movements using motivating content. Motion analysis module 162 optionally and preferably provides visualization of the kinematic parameters during a movement customized by the therapist or a movement from a list of predefined movements. Motion analysis module 162 optionally and preferably analyzes quality and confidence of the tracking data.

Kinematic parameters for each joint is optionally extracted from the patient motor calibration procedure or from dedicated patient assessment activity, optionally by tracking engine 112 but alternatively by motion analysis module 162. In the latter instance, motion analysis module 162 is optionally combined with tracking engine 112.

The kinematic parameters to be assessed may optionally include but are not limited to range of motion for each joint, reaction time, accuracy and speed. Optionally, the kinematic parameters are compiled in a graphical report available through a user display (not shown).

Functional assessment module 164 preferably records movement while operating standard assessment processes. Functional assessment module 164 preferably includes but is not limited to the following assessments: ARAT (action research arm test), FMA (Fugl-Meyer assessment) and WMFT (Wolf Motor Function Test). The results of the data collected with the assessments is optionally compiled in a graphical report available through a user display (not shown).

Cognitive assessment module 166 preferably provides at least a neglect analysis, including but not limited to the following settings: standard defined amount of targets/distractors; standard defined type of targets/distractors; standard defined spatial extension; and standard defined target distribution. The performance of the patients triggers default parametrization for the patient activity content regarding the cognitive aspect.

FIGS. 2A-2D show an exemplary, illustrative, non-limiting configuration of a mobile, table based system for supporting rehabilitation according to at least some embodiments of the present disclosure. As shown, a mobile table based system 200 features a display 202 for manipulation by a subject, who may for example be in a wheelchair, as shown with regard to a subject 212. Display 202 is mounted on the frame of system 200 so that visual information on display 202 is visible to subject 212.

Subject 212 is seated, whether in a chair or wheelchair, in front of a table 208. Table 208 sets a minimum plane, above which subject 212 performs one or more gestures. Optionally subject 212 may rest his or her hands and/or arms on table 208. Table 208 is also attached to the frame.

Subject 212 performs one or more gestures, which are detected by a camera 206. Camera 206 is optionally attached to the frame of system 200 or alternatively may be attached directly to display 202 or to a holder for display 202. Such an attachment optionally enables the base pillar to be shorter, such that, without wishing to be limited by a closed list, system 200 would be easier to transport and would have greater stability.

Preferably camera 206 features an image based camera and a depth sensor, such as a TOF (time of flight) sensor. The image based camera preferably features an RGB (red, green, blue) camera. The data from camera 206 is then communicated to a computer 214, which detects the gestures of subject 212 and which changes the visual information shown on display 202 accordingly. For example and without limitation, the gestures of subject 212 may optionally be used to play a game; the state of the game and the effects of the gestures of subject 212 are determined by computer 214 which adjusts the displayed information on display 202 accordingly.

A therapist or other individual may optionally adjust one or more aspects of the therapy, or gameplay, or otherwise control one or more operations of computer 214, through a controller 204. Controller 204 is optionally a touch screen display for example, such that information about the therapy and/or operation of computer 214 may be displayed on controller 204. Controller 204 is optionally attached to the frame of system 200. Optionally, controller 204 is attached to the same pillar support as display 202. Optionally camera 206 is attached to the same pillar support.

System 200 is movable due to rollers or wheels 210, which are mounted on the frame. Wheels 210 optionally have brakes to prevent unwanted movement.

Optionally the electronics of system 200 are powered through UPS and Battery but alternatively such power is provided by an isolation transformer.

FIGS. 3A-3D show an exemplary, illustrative, non-limiting configuration of another table based system for supporting rehabilitation according to at least some embodiments of the present disclosure. Items with the same number as for FIGS. 2A-2D plus 100 have the same or similar function as the corresponding item in FIGS. 2A-2D. For example, reference number "300" indicates a system 300 in FIGS. 3A-3D.

System 300 is similar to system 200, except that instead of wheels, a plurality of fixed feet 320 are present instead.

FIGS. 4A-4D show an exemplary, illustrative, non-limiting configuration of a system that is suitable for a subject in a bed, for supporting rehabilitation according to at least some embodiments of the present disclosure. Items with the same number as for FIGS. 2A-2D plus 200 have the same or similar function as the corresponding item in FIGS. 2A-2D. For example, reference number "500" indicates a system 500 in FIGS. 5A-5D.

System 500 is similar to system 200, except that the frame is adjusted so that system 500 is suitable for a subject 522 who is in a bed.

Figure 5:
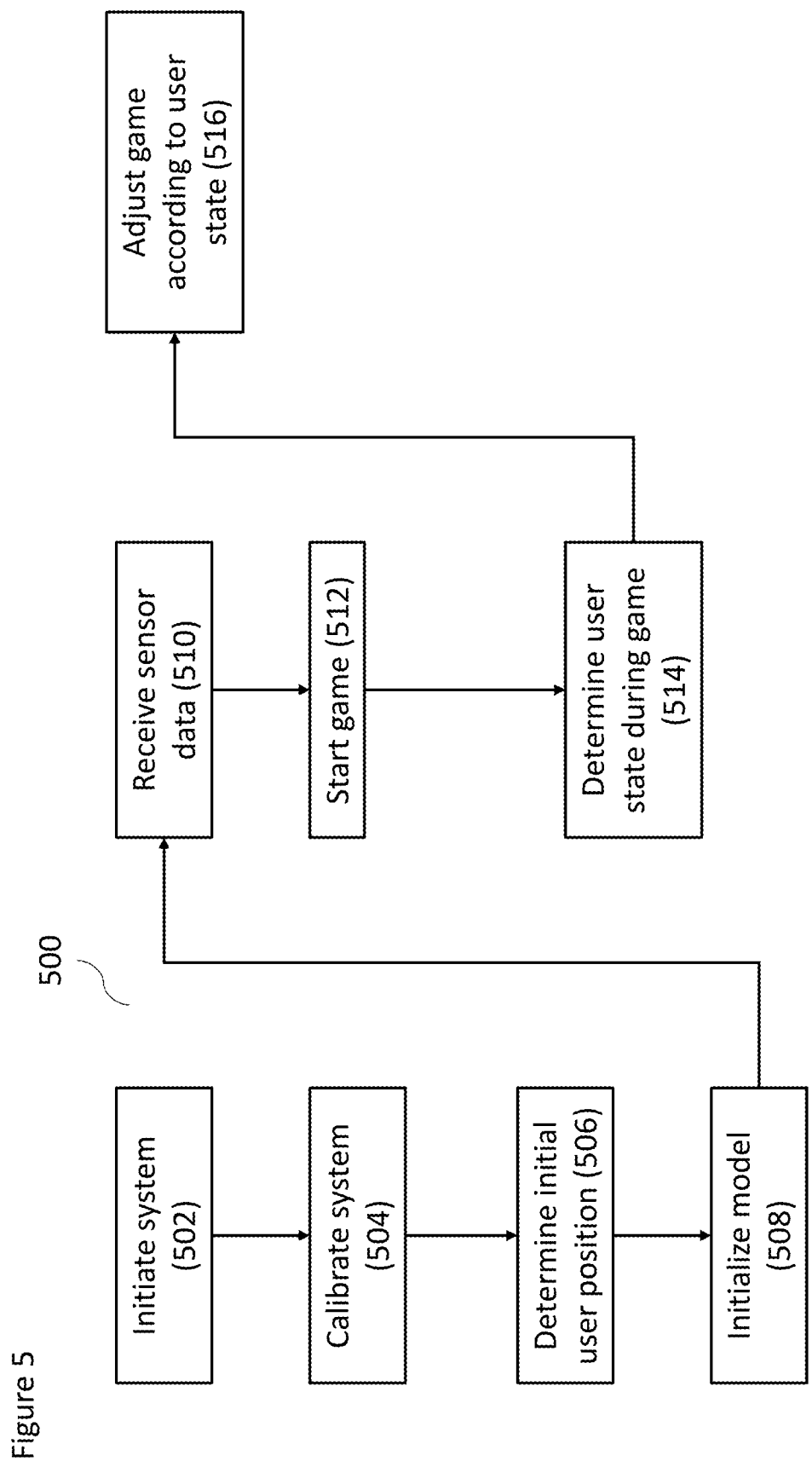
FIG. 5 shows a non-limiting example of a method for performing rehabilitation and/or training of the user, optionally performed with the systems of FIGS. 1A-1C, according to at least some embodiments of the present disclosure.

FIG. 5 shows an exemplary, illustrative non-limiting method for tracking the user, optionally performed with the system of FIG. 1, according to at least some embodiments of the present disclosure. As shown, at 502, the system initiates activity, for example, by being powered up (i.e., turned on). The system can be implemented as described in FIG. 1 but may also optionally be implemented in other ways. At 504, the system performs system calibration, which can include determining license and/or privacy features. System calibration may also optionally include calibration of one or more functions of a sensor.

At 506, an initial user position is determined, which (in some embodiments), is the location and orientation of the user relative to the sensors (optionally at least with respect to the camera and depth sensors). For example, the user may be asked to or be placed such that the user is in front of the camera and depth sensors. Optionally, the user may be asked to perform a specific pose, such as the "T" pose for example, in which the user stands straight with arms outstretched, facing the camera. The term "pose" relates to position and orientation of the body of the user. Preferably the gesture(s) of the user are calibrated in order to determine the range of motion and capabilities of the user, for example as described with regard to U.S. patent application Ser. No. 15/849,744, filed on 21 Dec. 2017, owned in common with the present application and incorporated by reference as if fully set forth herein.

Optionally, user calibration may comprise determining compensatory actions. Such actions occur due to motor deficit, causing the patient to involve a portion of the body in a movement which would not normally be involved in that movement. For example, a study by Aprile et al. ("Kinematic analysis of the upper limb motor strategies in stroke patients as a tool towards advanced neuro-rehabilitation strategies: A preliminary study", 2014, Biomed Res Int. 2014; 2014:636123), found that when reaching for an object, some patients showed reduced arm elongation and trunk axial rotation due to motor deficit. For this reason, as observed, the patients carried out compensatory strategies which included trunk forward displacement and head movements.

Table 1 below provides a non-exhaustive list of a few examples of such movements.

TABLE 1

| Compensatory Movements | | |
|---|---|---|
| Compensation | Happening during | Measurement |
| Trunk forward displacement | forward hand movement | angle of forward flexion of the trunk or both shoulder forward displacement |
| Trunk lateral displacement | hand movement to the side | angle of lateral flexion of the trunk or both shoulder lateral displacement |
| Trunk rotation | hand movement to the side | angle of axial rotation of the trunk or frontal distance between both shoulders |
| Shoulder elevation | hand elevation | displacement of the shoulder (rotation center) to the top |
| Shoulder abduction instead of flexion | forward hand movement | shoulder elevation angle in the lateral plane instead of frontal plane |
| Elbow flexion (absence of elbow extension) | hand movement away from the body (reaching) | elbow flexion |

Compensatory movement tracking and feedback is discussed further below in relation to FIGS. 11A-16C.

At 508, a model is initialized. This model features a model of a human body, configured as only a plurality of parameters and features, such as a skeleton, joints and so forth, which are used to assist in tracking of the user's movements. At 510, sensor data is received, such as for example, one or more of depth sensor data and/or camera data. At 512, the game is started and the user begins to interact with the game, for example by performing one or more movements. As previously described, the range of motion and capabilities of the user are preferably determined in advance, so that the movements performed by the user can be correctly assessed.

At 514, the state of the user is determined with regard to the user's movements. Optionally, the sensor data can be mapped onto the previously described body model, e.g., the body model features an articulated structure of joints and a skin defined by a mesh of vertices that are soft-assigned to the joints of the model with blending weights. In this way, the skin can deform accordingly with the body pose to simulate a realistic human shape and the user's movements can be correctly analyzed. Optionally, such analysis is performed with regard to PCT Application No. IB2018/000171, filed on 7 Feb. 2018, owned in common with the present application and incorporated by reference as if fully set forth herein.

The state of the user may optionally relate to the ability of the user to perform one or more movements, and/or any improvements in such an ability as compared to a previous session. Such an ability may optionally also be compared to an "ideal" model of normal human function, for example to determine whether the user has any functional deficits. Alternatively, for example with regard to training, such an ability may optionally be compared to a desired future state of the user. As a non-limiting example, such a desired future state may optionally relate to an improvement in one or more functions, or to a model of an "ideal" improved human functional state.

In stage 516, the game play is preferably adjusted according to the state of the user. For example, if the user has one or more functional deficits, then game play is optionally adjusted to be rehabilitative and useful with these deficits. On the other hand, for training purposes, game play may optionally be adjusted to induce the user to move in the direction of the desired improved state.

Figure 6A:
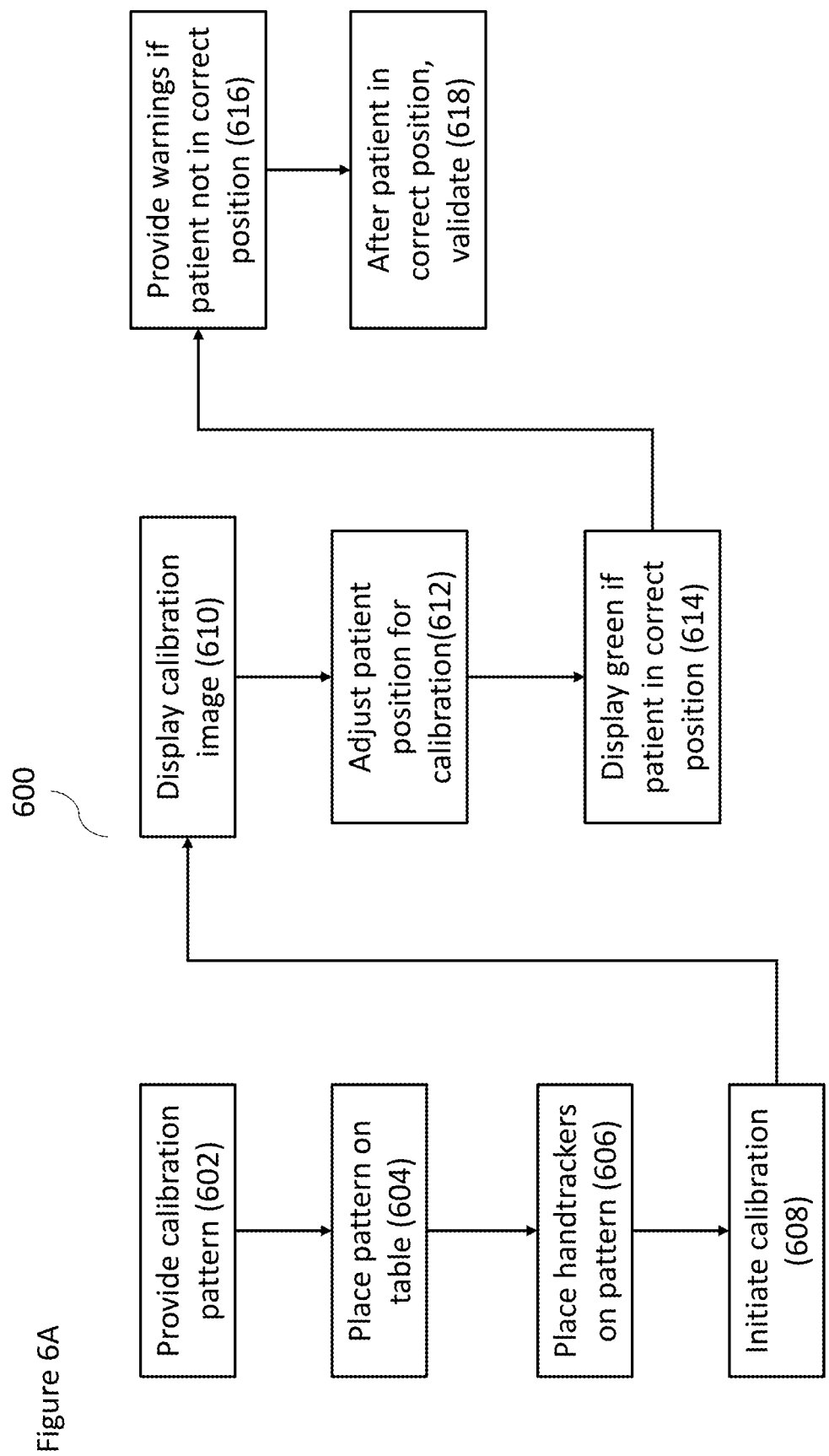
FIG. 6A shows an exemplary, illustrative, non-limiting method for patient table position calibration with the calibration pattern or with the ToF camera, according to at least some embodiments of the present disclosure.
Figure 6B:
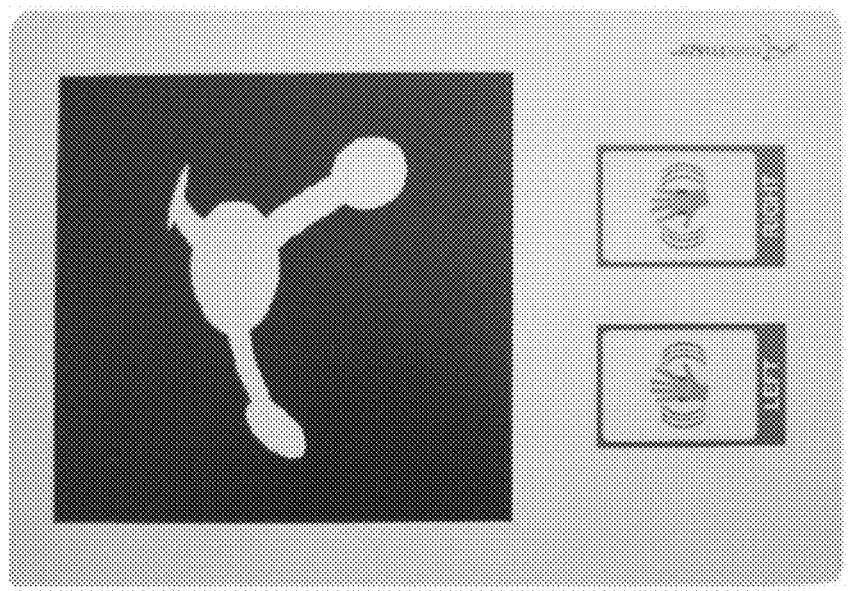
FIG. 6B shows an exemplary calibration pattern.

FIG. 6A shows an exemplary, illustrative, non-limiting method for patient table position calibration with the calibration pattern or with the ToF camera, according to at least some embodiments of the present disclosure; FIG. 6B shows an exemplary calibration pattern.

In stage 602, a calibration pattern device is provided, as shown with regard to FIG. 6B in a non-limiting example. The calibration pattern corresponds in this example to a large black square with a shape on a A4 format detectable by the camera and 2 HandTrackers images to correctly position the HandTrackers during the calibration. The handtrackers are markers attached to or associated with the hands of the patient.

In stage 604, the Calibration Pattern is placed flat on a horizontal Table between the Patient and the Camera inside the field of view of the Camera. In stage 606, in case of HandTrackers utilization, place the HandTrackers on the Calibration Pattern spots respecting the color codes and labels.

In stage 608, calibration is initiated, for example by selecting the calibration function through the user interface. Optionally the camera and the handtrackers can be calibrated separately.

In stage 610, a calibration image is displayed, optionally in a Body Tracking window with an overview of a Live Calibration Image displayed, which shows the image with the detected Markers captured by the Camera. The Body Tracking algorithm will automatically detect the body Markers associated to the joints of the person in front of the Camera. In stage 612, the position of the patient is adjusted for correct calibration, so that the joints of the "skeleton" (figure abstraction) are in a correct position.

In stage 614, when all the skeleton's joints are associated appropriately with the detected Markers from the Camera Live Feed, they are displayed in green. Objects similar to the Markers are detected and highlighted as blue circles. These objects are preferably removed from the field of view of the Camera to avoid confusion in the Markers detection.

In stage 616, one or more warnings are provided, if the patient is not in the correct position. Non-limiting examples of such warnings are given below in Table 2.

TABLE 2

Warnings

| Warning | Description | Calibration |
|---|---|---|
| Markers Detection | | |
| x/6 markers detected | The x represents the number of detected Markers. Please check that the markers are switched on and attached to the patient and that the patient is in the field of view of the tracking camera. Ensure that the markers are well visible to the camera, and not occluded by the patient. | Blocked |
| Markers Position | | |
| Check Markers Placement | Please check that all the markers are attached to the patient's joints in the correct locations, as shown. Some markers might be exchanged between the right and left side of the patient. | OK to proceed |
| Patient Position | | |
| Patient not properly positioned | Please check that the patient is in the field of view of the tracking camera. Ensure that the patient is in the middle of the calibration image. | Blocked |
| Turn camera right | The patient is too far on the right. Please turn the tracking camera to the left to have the patient in the middle of the calibration picture | Blocked |
| Turn camera left | The patient is too far on the left. Please turn the tracking camera to the right to have the patient in the middle of the calibration picture | Blocked |
| Turn camera down | The patient is too far up in the image. Please move the tracking camera down to have the patient in the middle of the calibration picture | Blocked |
| Turn camera up | The patient is too low, the shoulders may disappear in the image. Please turn the tracking camera up to have the patient in the middle of the calibration picture | Blocked |
| Camera position | | |
| Camera not properly positioned | Please check that the camera is well placed to have the patient in the middle of the calibration picture. | Blocked |
| Camera too close | Please move the camera away from the patient of move the patient away from the camera | Blocked |
| Camera too far | Please move the camera closer to the patient or move the patient closer to the camera | Blocked |
| Camera too high | Please move the camera to have the patient centered in the calibration picture | Blocked |
| Camera too low | Please move the camera to have the patient centered in the calibration picture | Blocked |

In stage 618, after the patient is in the correct position, validation is indicated, for example by selecting validation through the user interface. Optionally validation of the calibration pattern occurs automatically. If not, a warning is issued (for example, if the pattern isn't visible to the camera).

Figure 7:
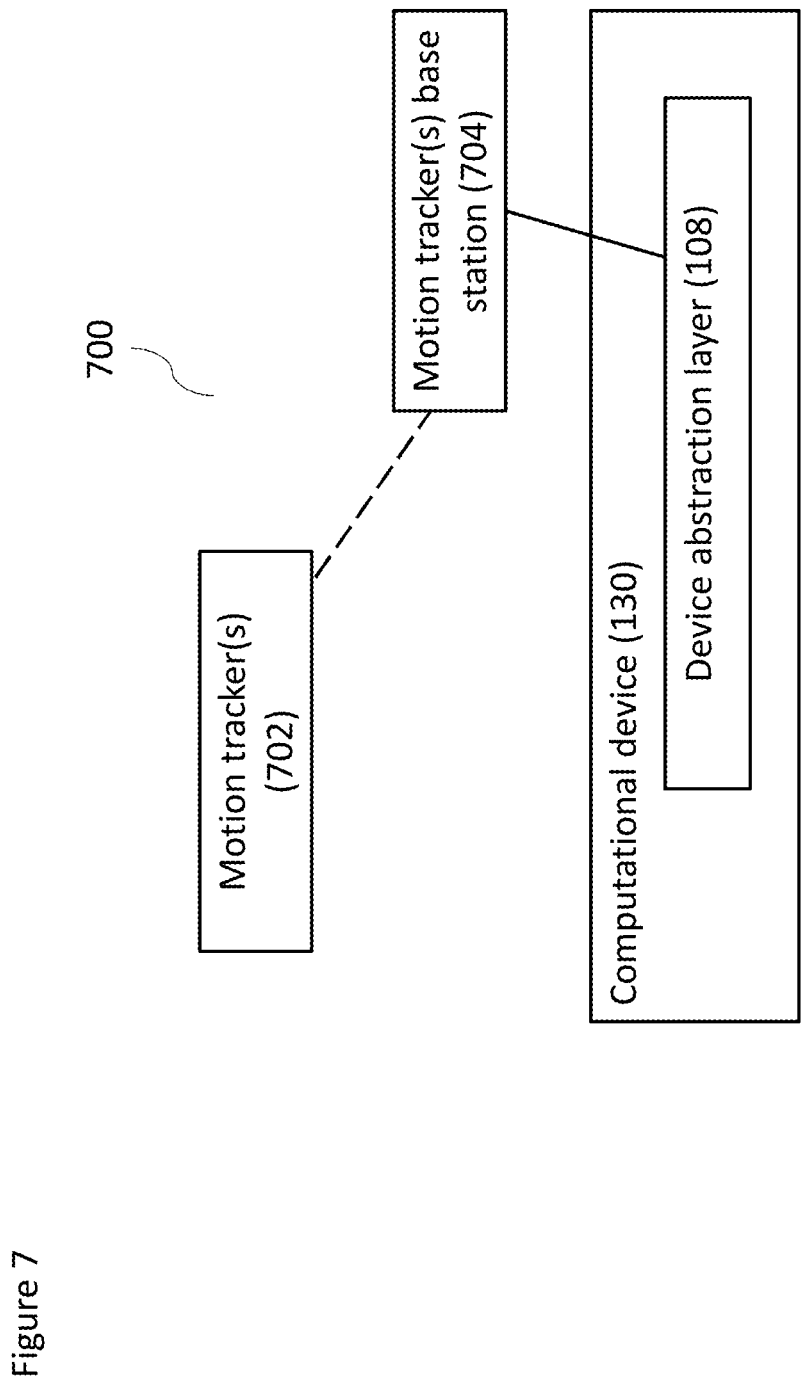
FIG. 7 shows a portion of an exemplary, illustrative, non-limiting system for motion tracking according to at least some embodiments of the present invention.

FIG. 7 shows a portion of an exemplary, illustrative, non-limiting system for motion tracking according to at least some embodiments of the present invention. Additional components from any of systems shown in FIGS. 1A-1C may also be incorporated to the system, even if not explicitly shown.

As shown in a system 700, one or more motion tracker(s) 702 are provided. Preferably these motion tracker(s) 702 are wireless and are also preferably inertial sensors and/or incorporate such inertial sensors. They may for example be attached to a subject with a strap or other attachment, and/or may be provided in clothing or other wearables. Each motion tracker 702 is in communication with a motion tracker base station 704, which is able to receive motion tracking information from motion tracker 702 and to provide this information to device abstraction layer 108. Communication between motion tracker base station 704 and computational device 130 may optionally be wired or wireless.

Motion tracker(s) 702 and motion tracker base station 704 may optionally be implemented according to the Xsens "ATWINDA" system for example. Motion tracker(s) 702 may be used for body tracking and/or tracking of specific parts of the body, such as for hand tracking for example. Motion tracker(s) 702 may be used alone or in conjunction with the previously described markers and/or with markerless tracking.

Referring now to FIGS. 8A-8E, in some preferred embodiments, system calibration, for example corresponding to a portion of system calibration of step 504, some other step, or as a separate step, can include calibration of a workspace area or 2-dimensional region within the virtual environment that lies on a plane on which elements (e.g., targets, distractors, and the like) are placed. Calibration can be done using adjustment of the location of vertices of the area and shape of the edges, including the curve of the edges. In some embodiments, the workspace is dissected by a "magnetic" axis. Each end of the axis is adjustable so that the workspace can be dissected at any angle. In some embodiments, the workspace can include a "magnetic" target center.

In therapeutic virtual reality systems, working areas are normally determined by the patient's range of motion. If a region is outside the patient's range of motion, the region falls outside the working area. A typical calibration process will include determining a maximal radial distance at a number of points of a patient range of motion from a resting position and setting a workspace region having vertices based on those points. Motion tracking information can be used to determine the location of points as the patient moves a body part. The typical range-of-motion calibration suffers from a few drawbacks. It does not account for compensatory movement of the patient and, therefore requires concurrent intervention to prevent any compensation of the patient. Without intervention, the calibration is not be reliable. Further, it relies on a patient extending to a range of motion suitable for the rehabilitation of that patient at the beginning of the therapy. At the beginning of therapy, the patient often is unable or not motivated to extend to a suitable range of motion. Conversely, a proper range of motion reached by a patient may require expending energy that may be required for the therapy itself, thus, undermining therapeutic goals.

Embodiments of the present invention solve these problems by providing workspace area configuration of the size, location, and distribution probability for the workspace area. Benefits include the lack of requirement of patients to expend energy pre-activity during calibration, customization of workspace based on the progress of the patient from exercise to exercise without recalibrating the entire VR system or a greater portion of the VR system. Embodiments of the present invention also allow for a faster calibration process.

Figure 8A:
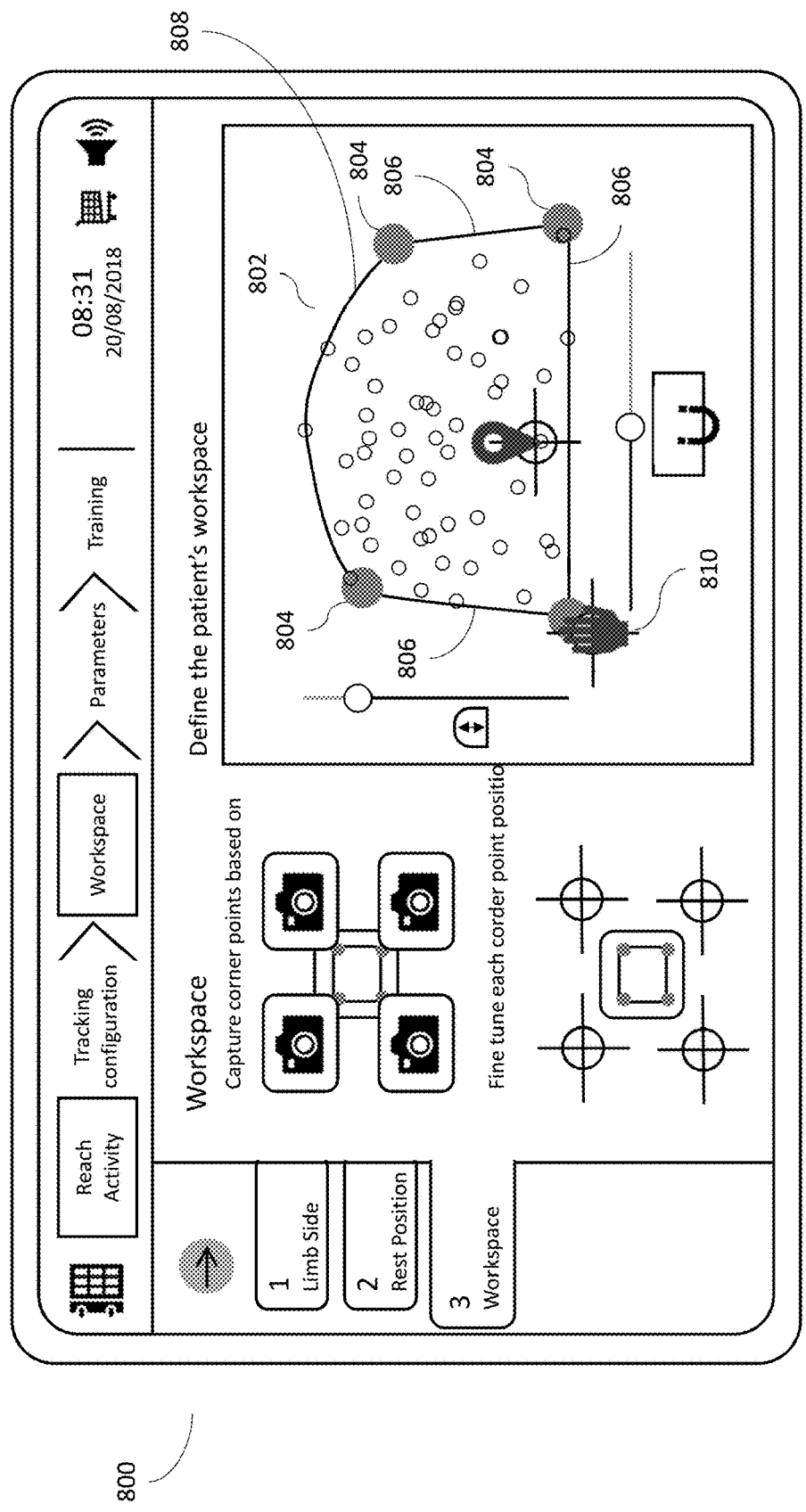
FIGS. 8A-8E illustrate an exemplary user interfaces for calibrating a user workspace in accordance with embodiments.

Referring to FIG. 8A, an exemplary illustration of a display 800 for calibrating a workspace area 802 is shown. In preferred embodiments, display 800 is presented on a first display for a therapist or other person to view a workspace area calibration interface. An exemplary workspace calibration interface can include four vertices 804 marking a workspace area 802. In some preferred embodiments, three or more than four vertices can be included. The therapist user can adjust the position of the vertices to define an active area in which interactive elements of an activity can appear. Such interactive elements could include, for example, a target for a reach exercise, a path for the user to follow for a reach exercise, distractors. The vertices are preferably adjustable in two dimensions so that the area can take various sizes and account for a patient's range of motion and therapeutic needs. The displays can be a monitor, head-mounted display, or other type of display.

Workspace area 802 includes four sides, a bottom and left and right sides 806, and a top side or edge 808. The number of sides in a workspace area is dictated by the number of vertices. In preferred embodiments having a workspace area with four sides, the bottom and connected left and right sides 806 are defined by straight lines and the top edge 808 is defined by a curve. The curve path defining the top edge 808 is preferably based on a quadratic or some other curvilinear equation with the peak and ends of the curve adjustable. For example, the two vertices 804 that intersect the curve are preferably adjustable in the y- and x-axes to adjust the location of the right and left ends of the curve. Also, the peak of the curve is preferably adjustable in both the x-axis and y-axis. In this way, the workspace area can be adjusted to accommodate the patient's reach throughout the patient's range of motion and to allow for the placement of targets or other virtual environment elements to appropriately exercise the user.

Figure 8B:
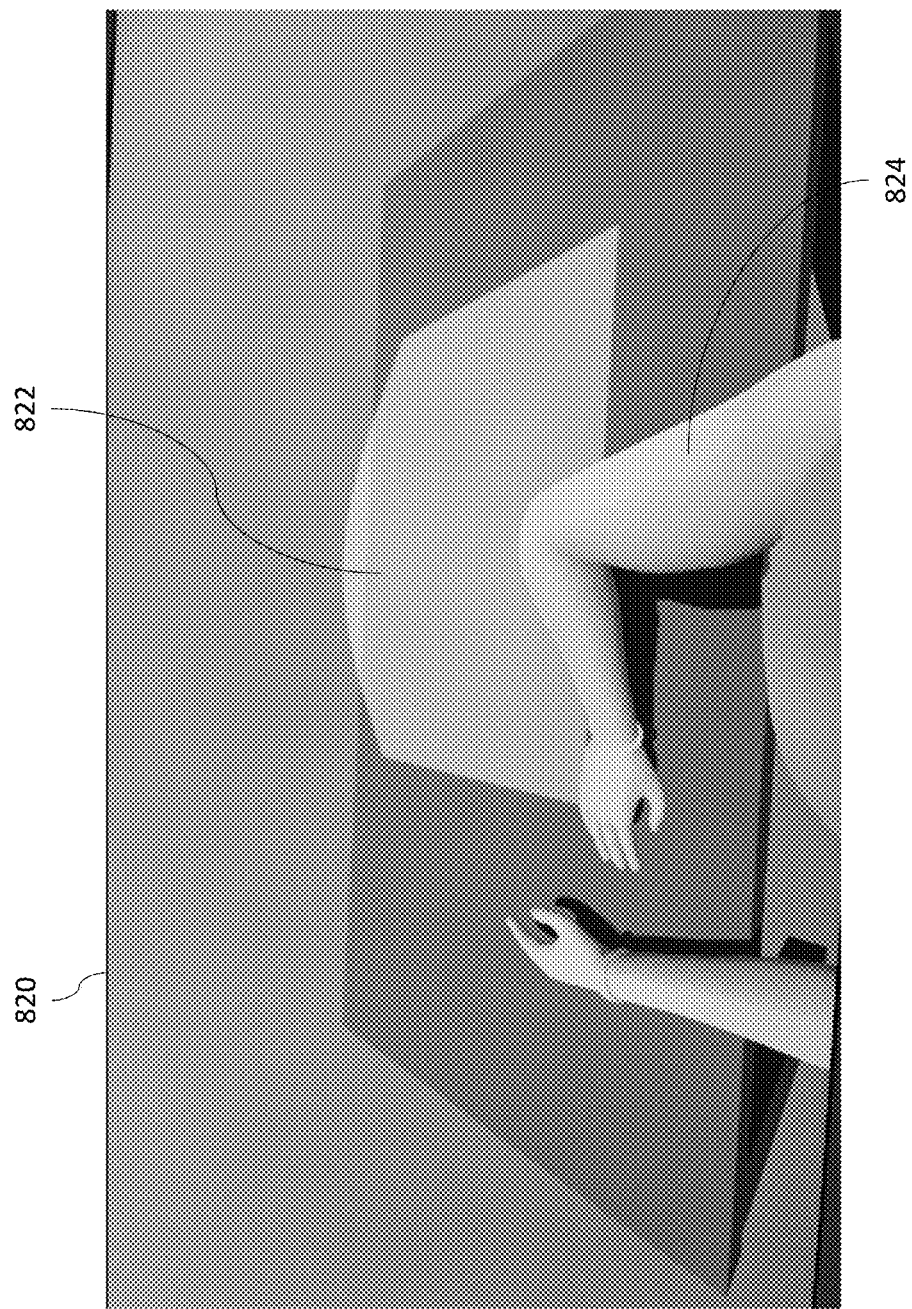

In preferred embodiments, the system includes two displays. A first display, as illustrated in FIG. 8A, can be used by a user to configure the workspace. A second display 820, as illustrated in FIG. 8B, can be used by the patient to assist in configuring the workspace. For example, the tracking system can be used to determine the location of the patient's hand or other body part and overlay a hand avatar 810 or avatar of another body part on the workspace are calibration or configuration interface. Preferably, vertices and top edge curvature are initially located based on patient hand (or other body part) tracking. For example, the top edge curvature can be fitted to a path of movement of the user's hand (or other part). The second display 820 can include an element representing the workspace area 822 as the workspace area is being configured or calibrated. In the example shown in FIG. 8B, the second display as seen by the patient also includes a user avatar 824 showing that patient's movements to help set the vertices of the workspace area. Preferably, the first display allows the user to adjust the workspace area vertices and other dimensions as the patient motion and location is tracked to allow for configuration by the user with the tracking animation displayed.

In preferred embodiments, the workspace area is defined in two stages. First, the patient range of motion is used to determine vertices and, second, the workspace area is modified by another user. Motion tracking data of the placement of user body at a vertex location is received and used to define each vertex. For embodiments with a workspace area defined with four vertices for training of upper limbs the user can move a hand to a close-left, close-right, far-left, and far-right locations and the motion tracking data received at the time of the hand placement at those locations is used to define the vertices.

Figure 8C:
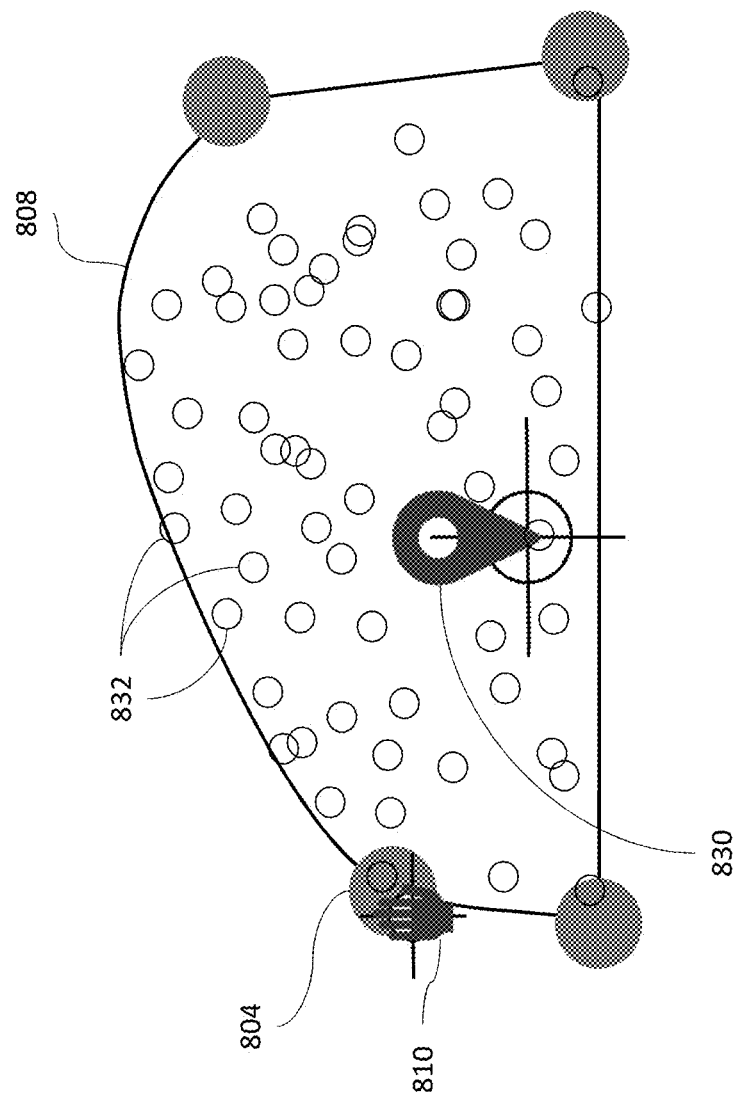

During calibration, a distribution probability of targets can be determined. For example, FIG. 8C illustrates an exemplary workspace area configuration interface in accordance with embodiments. A resting location or starting position 830 for an activity for the patient is shown. The current position of the patient's hand is animated in an avatar 810 over a vertex 804 of the workspace area. A distribution probability is illustrated by potential location markers 832. In the illustration shown in FIG. 8C the probability distribution is limited to the workspace area. Preferably, the x and y coordinates of a potential location are modulated to fit within the bounds of the vertices and edges, including the top edge curve 808. In accordance with preferred embodiments, the number of potential target locations can also be adjusted.

Figure 8D:
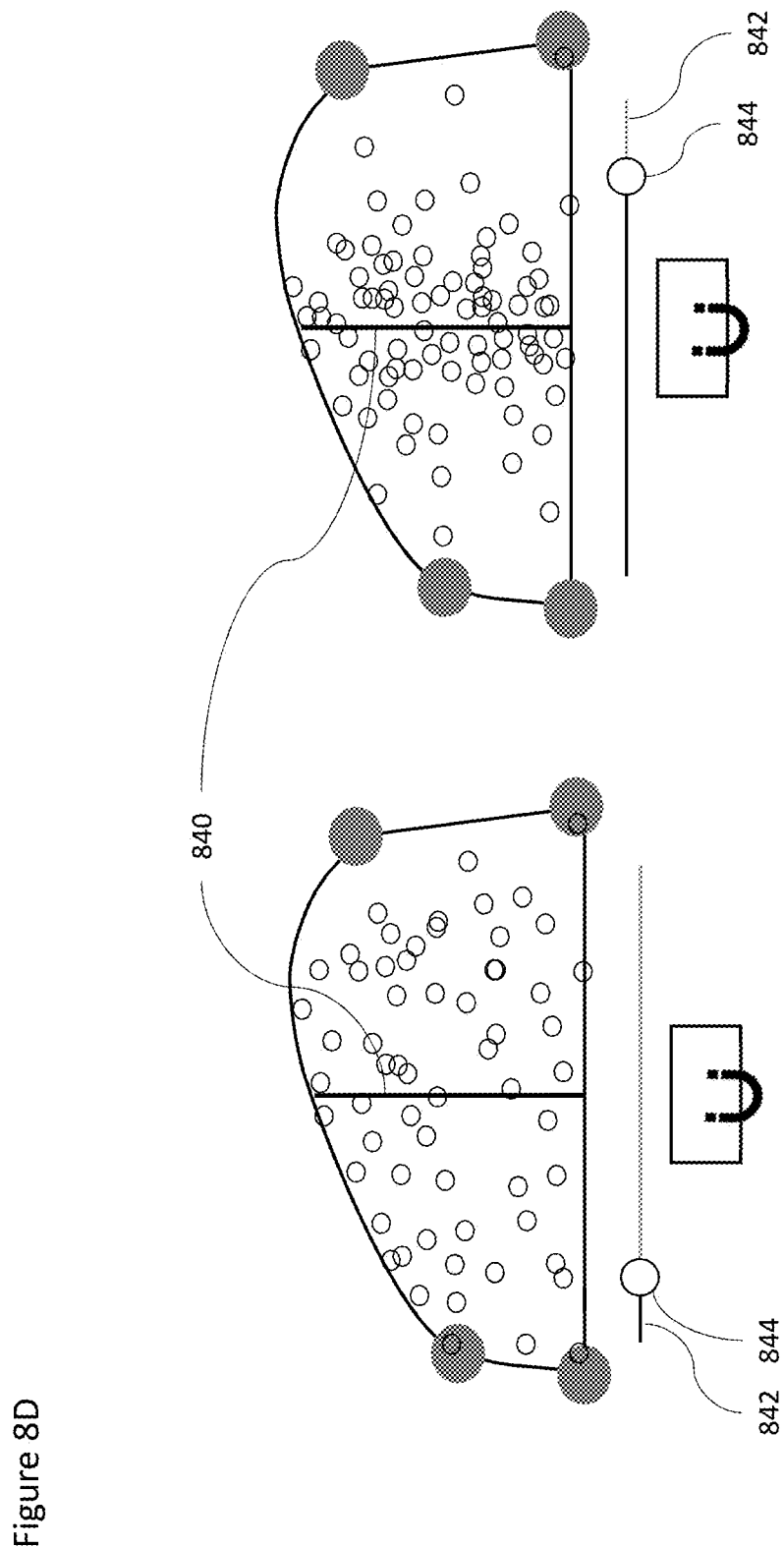

In some preferred embodiments, potential target locations are distributed according to a bell curve distribution around an axis that intersects the workspace area or around a point in the workspace area. For example, as illustrated in FIG. 8D, the potential target locations are determined using the magnetic axis 840 to weight the distribution and used as input to different types of activities. Preferably the distribution is limited to the defined 2-dimensional area. The distribution can be weighted with different standard deviations to keep the distribution closer to the axis or more diffuse. For some activities that require a single target at any given time (e.g., a reach exercise in which the patient is directed to reach toward a target) one of the potential target locations can be selected at random from the distribution. For activities that require, more than one target, a plurality of targets can be selected, including selecting one or more of the potential target locations as targets and one or more of the potential target locations as distractors or placements for other interface elements. For some activities that require multiple targets, multiple locations can be selected at random from the distribution or the probability distribution can be determined multiple times with one or more targets selected from each distribution. Final target locations selected at random or by the therapist.

Figure 8E:
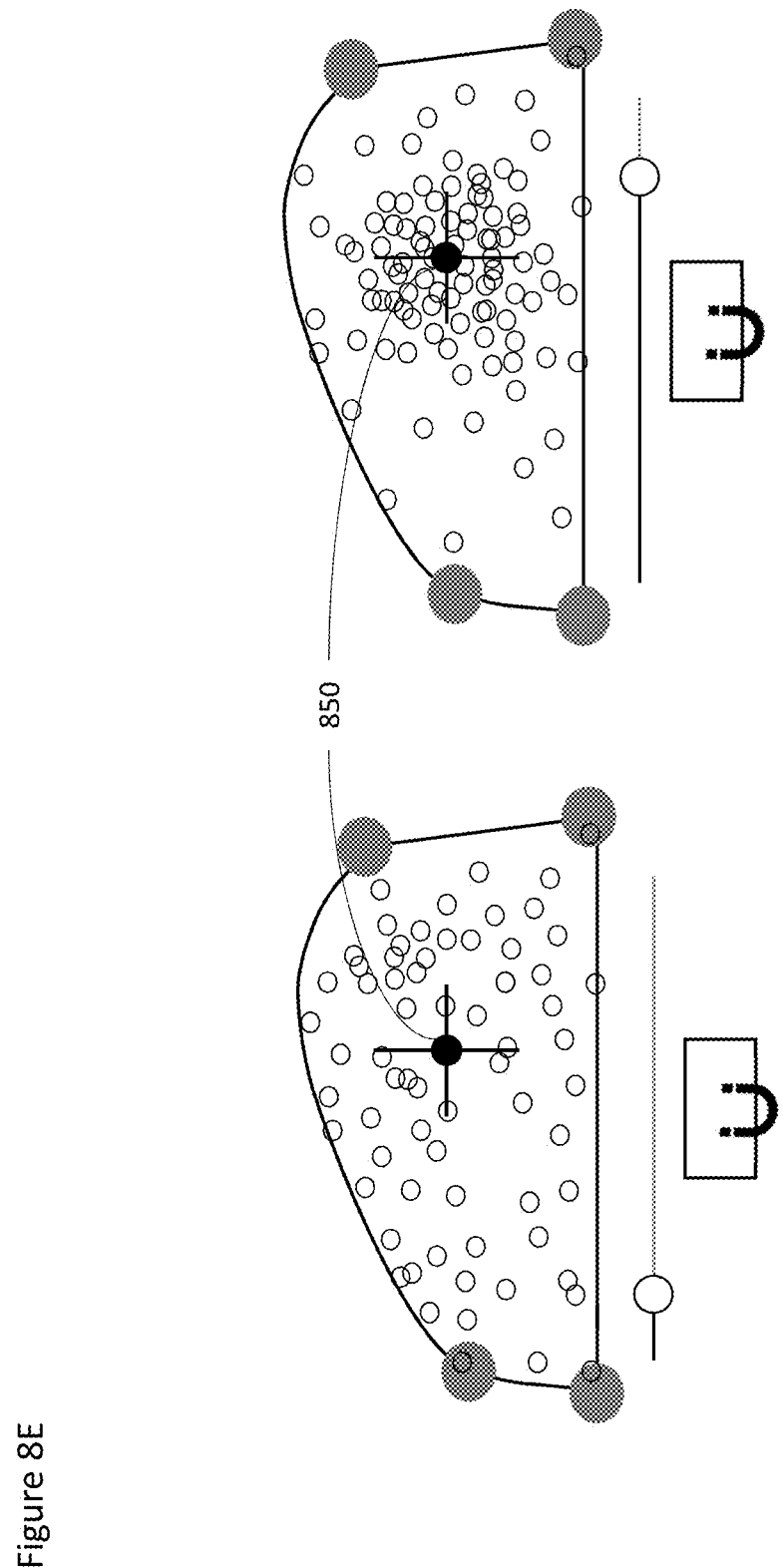

In accordance with preferred embodiments, the interface includes a slider 844 along an linear element 842 to adjust a standard deviation for configuring the distribution. Skilled artisans understand that other user interface elements can be used to implement a distribution adjuster that can be used to set a standard deviation for a distribution. As shown in FIG. 8E, a lower "magnetic" value (i.e., slider to the left of the adjuster in the image on the left) results in a larger standard deviation and more distributed potential locations and a higher "magnetic" value (in the image on the right) results in a smaller standard deviation and a distribution closer to the axis. In accordance with preferred embodiments, the axis can be rotated such that the distribution falls along both the x-axis and y-axis or just the y-axis as opposed to along just the x-axis as illustrated in FIG. 8D As illustrated in FIG. 8E, in some embodiments, potential target locations can be distributed around a single point 850 in the workspace area. For a single point, the potential target locations preferably are randomly located around the point with the radial distance of the potential target from the point weighted according to an adjustable standard deviation. For an axis, the potential targets are randomly located along the axis with the distance from the axis weighted according to an adjustable standard deviation. Preferably, a potential target is located within the workspace area and the maximum distance from the bottom axis of the workspace area is y(x) of the linear equation defining the top of the workspace area.

Figure 9:
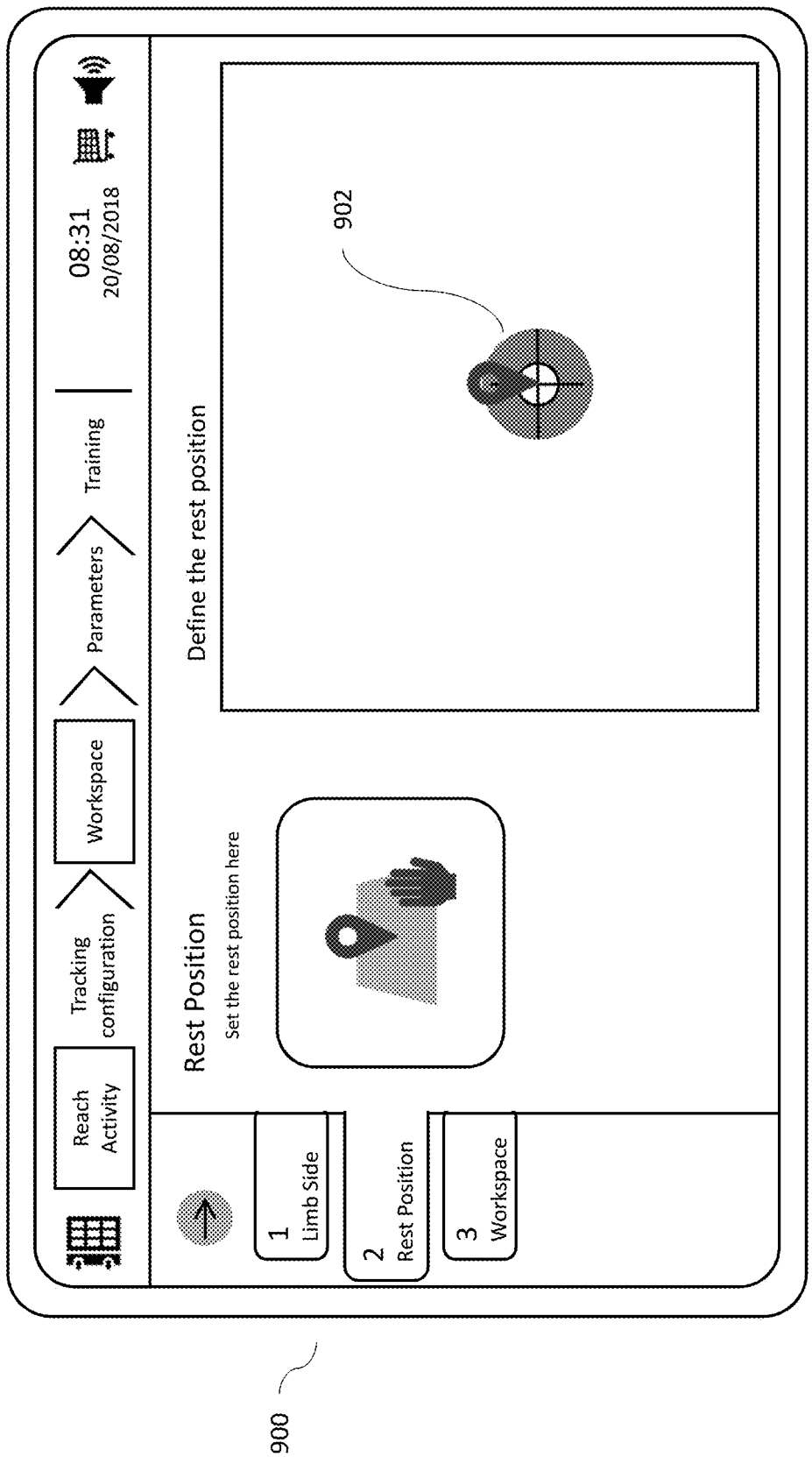
FIG. 9 illustrates an exemplary user interface of a first display used to configure or calibrate the system prior to an activity or exercise in accordance with embodiments.

Referring now to FIG. 9, an exemplary interface 900 of a first display used to configure or calibrate the system prior to an activity or exercise is illustrated. A rest position 902 can be set by a user for the user to reach or can based on the patient's position.

Figure 10:
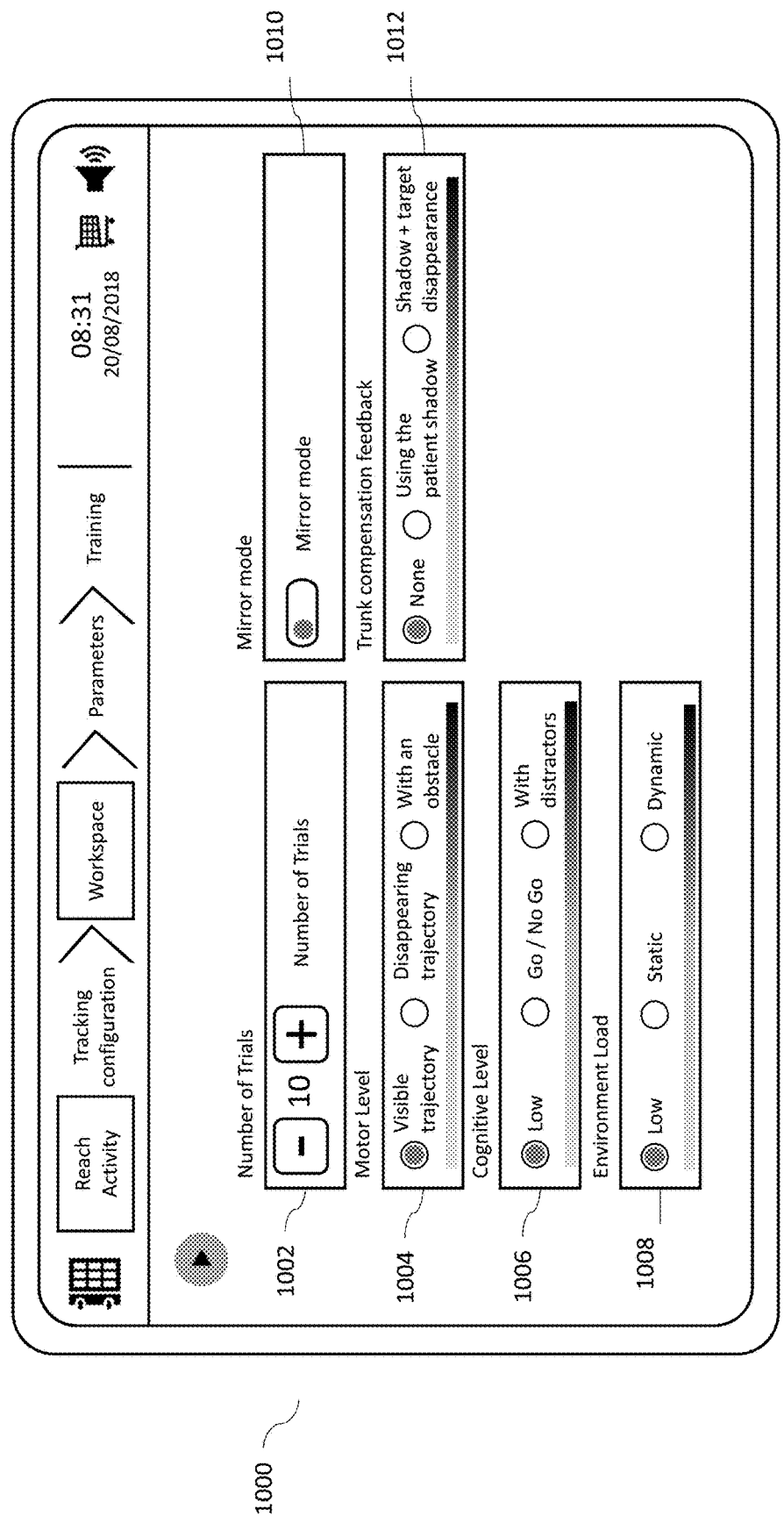
FIG. 10 illustrates an exemplary user interface for initializing other gameplay (or activity or exercise) parameters in accordance with embodiments.
Figure 14A:
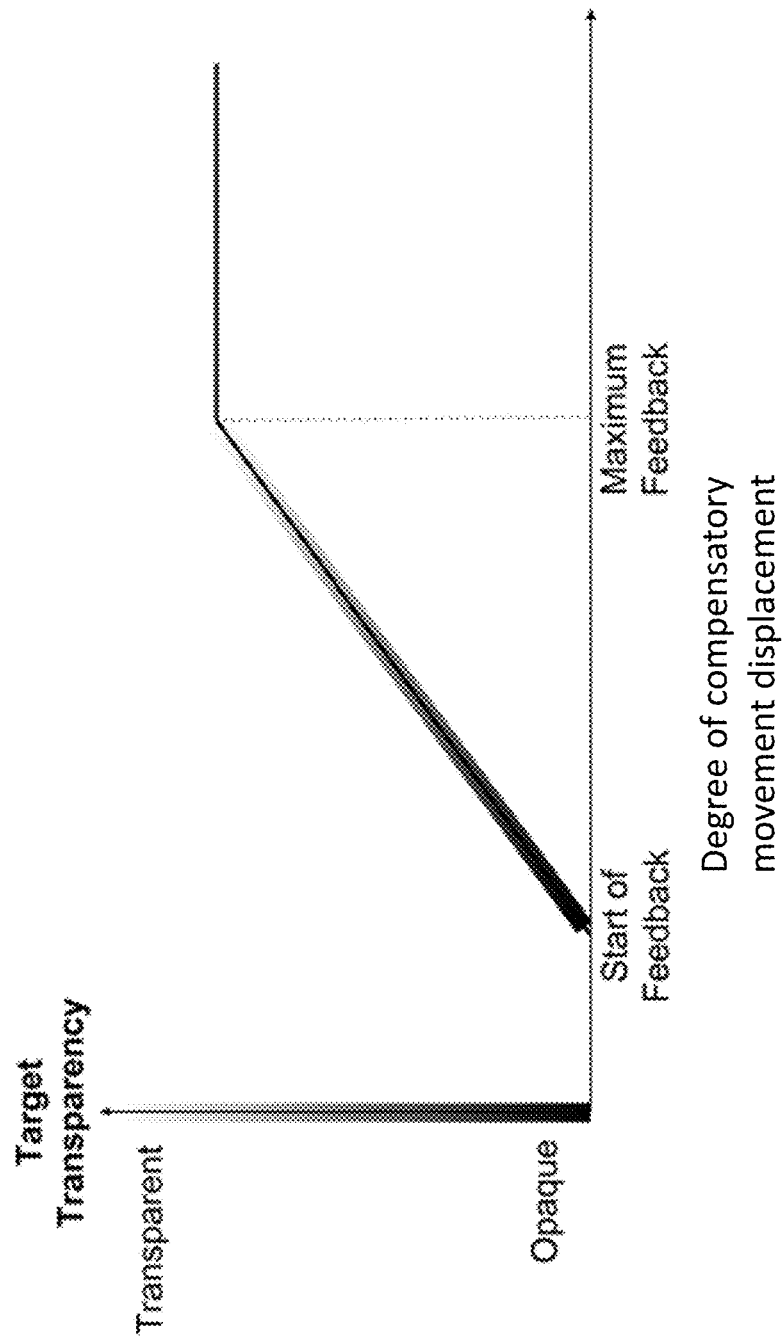
FIGS. 14A-14B illustrate exemplary charts representing compensatory feedback threshold levels and types of feedback in accordance with embodiments.
Figure 14B:
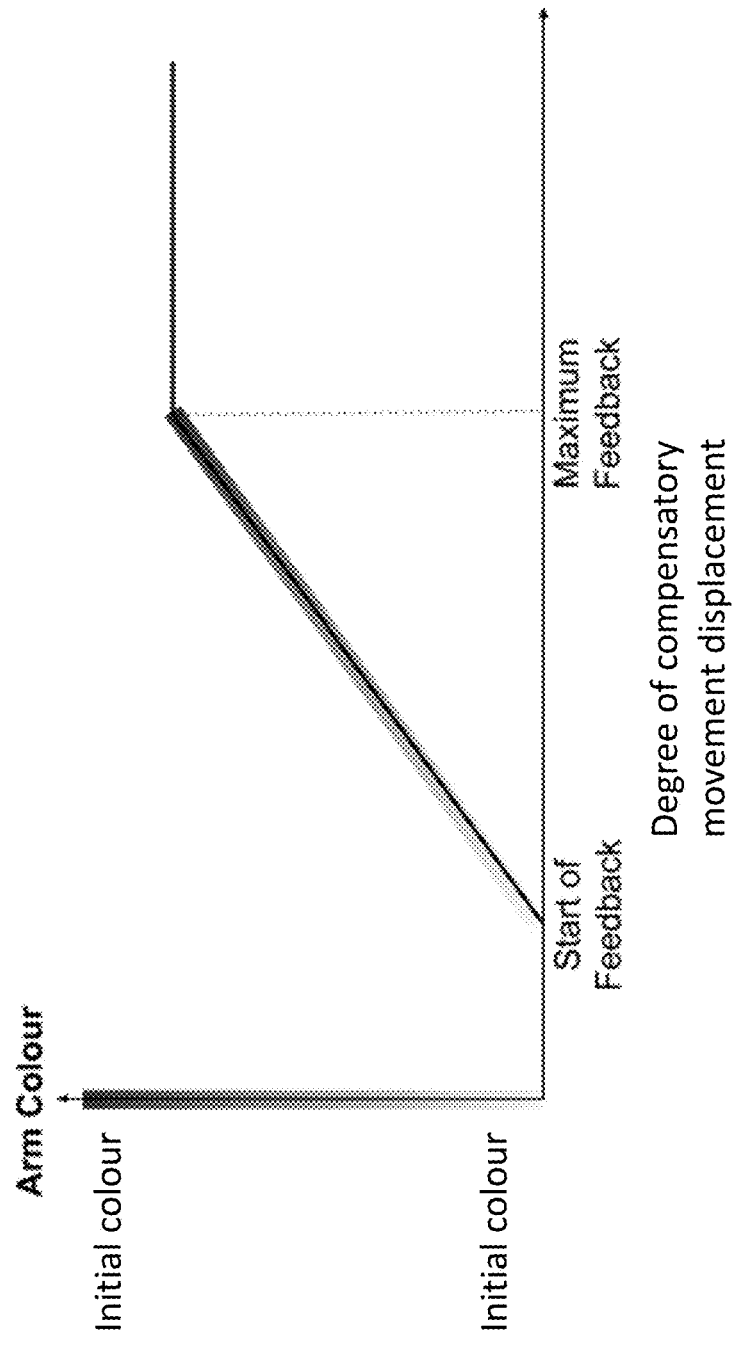

In FIG. 10, an exemplary interface 1000 for initializing other gameplay (or activity or exercise) parameters is illustrated. In accordance with preferred embodiments, such parameters include number of trials 1002, motor level 1004, cognitive level 1006, environment load 1008, mirror mode 1010, and compensation feedback 1012. Skilled artisans can appreciate that other parameters can be included and interfaces to set parameters can be further combined or separated. In some preferred embodiments, the method of FIG. 5 also includes receiving parameter data to initially configure gameplay.

In preferred embodiments, compensatory movements of a patient are determined and feedback is provided to the patient through one or more interfaces of the system (e.g., visual, audio, haptic, and the like). Such compensatory movement tracking and feedback can be done in, for example, step 514 from the method of FIG. 5, or as the user is tracked during a game or activity. In current devices and systems that track and provide feedback of compensatory movement, the feedback is provided outside the scope of gameplay or takes the form of changing the scope of gameplay. In the former case, current systems will display an avatar or other signaling image to the user indicating compensatory movement. Such an indication takes the user's attention away from the therapy or activity and, thus, reduces the efficacy of the activity and frustrates and confuses the user. In the latter case, current systems will change the rules or goals of the activity which similarly distracts or frustrates the user. Additionally, therapeutic goals and objectives become somewhat less clear and whether the user meets the goals and objectives. For example, U.S. Publ. Serial No. 20170231529A1 describes a system which provides a flashing lights and screens, audio, or a vibration as biofeedback. The inventors have found that patients presented with this type of extraneous stimulation distract the patient from the gameplay and reduce the effectiveness of the therapy. Other systems control compensatory movement using harnesses or through therapist interdiction.

Embodiments can include visual feedback as well as audio feedback or haptic feedback, depending on the activity and the available hardware. In preferred embodiments, compensatory movement feedback parameters are determined by patient-specific data and through workspace configuration. Parameters determined by workspace configuration are independent of patient-specific data. Feedback thresholds are determined through combination of patient-specific parameters and workspace configuration.

In preferred embodiments, compensatory movement feedback is provided at two or more threshold levels. More preferably, three or more levels of compensatory feedback are provided. At each level, another form of feedback is added. In some preferred embodiments, the particular type of or level of feedback given about compensatory movements used during the activity can be set by the therapist. As described further below, there are at least three levels of feedback:

Level 1: No feedback and the patient should be able to complete the given task in spite of a certain level of compensation below a minimum threshold.

Level 2: Integrated visual/auditory feedback—non-blocking patient's experience of the reach (does not affect the game play). The patient should be able to complete the task in spire of a certain level of compensation but feedback is provided as an integrated part of the activity. The feedback does not interfere with the movement controller or the game logic. Examples include graduated change of transparency or hue of an activity element (e.g., avatar shadow, target, target path, and the like) or graduated visual blocking of an activity element using another activity element (e.g., gradual blocking of target or target path with avatar). In preferred embodiments, the graduated change begins at the threshold of compensation for the level.

Level 3: Integrated visual/auditory feedback—blocking patient's experience of the reach which affects the game play. The patient is not allowed to complete the given task. Feedback is provided and interferes with the movement controller (e.g., a hand orientation only reacting on the wrist rotation for a wrist movement activity) or the game logic (e.g., a target disappears or becomes transparent in a reach activity) such that the task cannot be completed.

Feedback for Upper Limb Multiple Joint Exercises/Activities

Feedback indicating trunk forward flexion is a typical compensatory mechanism used during reaching activities to avoid arm use. Thus, in preferred embodiments that track forward trunk flexion, flexion is be measured by calculating the forward angle of the vector created by the L5 bone base and the skull bone base in the body model with respect to the vertical. Skilled artisans can appreciate that a body model used in tracking identifies bones of the vertebrae that can be used to determine forward trunk flexion and other bones, for example in the arm, to detect other types of compensatory movement.

For instance, the inventors were able to determine forward trunk flexion to provide effective integrated feedback using a basic body model that includes the following skeleton portions:
1. 3 vertebrae bones:
   i. sacrum
   ii. L5
   iii. T1
2. neck bone: skull
3. 2 scapular bones:
   i. l_clavicle
   ii. r_clavicle
4. 2 upperarm bones:
   i. l_upperarm
   ii. r_upperarm
5. 2 forearm bones:
   i. l_forearm
   ii. r_forearm As a reference, the location of a vertebrae in accordance with the above skeleton with respect to their anatomical bone correspondences is as follows:
1. sacrum: From the sacrum to L1
2. L5: From L1 to T6
3. T1: From T6 to C3
4. Skull: From C3 to a terminal point in the middle of the head.

The bones used to calculate the flexion were found by performing tests on healthy participants using the following protocol. The subject reaches in 5 directions (center, right, left and between) one after another. The reaching targets were placed at a distance equivalent to 90% (Valdés et al. 2016) of the arm length. This was be performed at three different heights (table height, shoulder height, eye level height). The eye height was estimated as 24.5 cm above shoulder height ~=eye height (50th percentile human shoulder to eye length). The inventors found from the results that preferable degrees of trunk flexion compensation feedback were 7% and 20%.

In instances where trunk flexion compensation is tracked, level thresholds of compensation are preferably at 7% and 20% degrees from the patient's rest position. In such an embodiment, from 0% to 7%, feedback indicates no compensation, at 7% up to 20% an initial feedback threshold begins, and at 20% a terminal threshold begins. In preferred embodiments, the initial feedback is provided at a gradient and is proportional to the degree or magnitude of compensation. At the initial threshold the activity goal is still achievable and while at the terminal threshold the activity goal is no longer achievable.

Exemplary feedback thresholds are described in the following Table 3.

TABLE 3

Feedback Thresholds (degrees)

| Rest Trunk Forward Flexion Position | Start of Feedback Threshold | Maximum Feedback Threshold |
|---|---|---|
| <=0° | 7° | 20° |
| >0° | Rest Position + 7° | Rest Position + 20° |

Referring to FIGS. 11A-11C, exemplary screenshots of a preferred embodiment with shadow or visual trunk feedback are illustrated. In FIG. 11A, no head or trunk avatar is shown to indicate no or minimal compensation. In FIG. 11B, a portion of a head avatar 1102 is shown which begins to block the target and target path for the user. In FIG. 11C, a further portion of a head avatar 1102 with visible shoulders obscures more of the target and target path to indicate further trunk flexion. In preferred embodiments, movement of the blocking avatar is smooth and tracks the movement of the user as, for example, trunk flexion increases or decreases. The blocking avatar becomes visible when a minimum threshold of compensation is made. At a maximum threshold of compensation is detected in the user, the avatar blocks the target and the user is prevented from reaching or achieving the target. In some embodiments. the avatar can appear as a shadow and can change color, preferably from light to dark, as flexion increases. In some embodiments, the avatar can appear with a level of transparency that increases to obscure the target and target path as flexion increases. Preferably, the level of transparency is 0 when the maximum threshold is reached.

Referring to FIGS. 12A-12C, exemplary screenshots of a preferred embodiment with target blocking are illustrated. In FIG. 12A, the target 1202 is shown with solid color to indicate no or minimal compensation along with a target path 1204 for the user to follow. In FIG. 12B, the target 1206 is shown partially transparent to indicate compensation above a minimal threshold level. In accordance with some preferred embodiments, path 1204 can also be shown partially transparent. In FIG. 12C, the target 1208 is shown completely or near-completely transparent to indicate compensation beyond a maximum threshold. At this stage the target is preferably unachievable by the patient. In some preferred embodiments, the target path 1204 can also be shown as completely or near-completely transparent. Preferably, the degree of transparency is smooth and changes as θ changes, as exemplified in FIG. 14A.

FIGS. 13A-13C illustrate exemplary screenshots and corresponding compensatory movement ranges of a preferred embodiment with that includes integrated feedback in the form of an avatar shadow. In FIG. 13A, the user 1300 exhibits no or minimal compensatory movement during a reach activity that asks the user to reach out to the target 1302 along a particular path 1304. On the display 1306 seen by the user during the activity, the avatar shadow 1308 of the avatar arms 1310 is a shade of gray to indicate compensatory movement within acceptable levels. In FIG. 13B, the user 1300 exhibits compensatory movement beyond an minimal threshold but not a maximum threshold. On the display 1306, the avatar shadow 1308 changes hue to reflect the level of compensation that corresponds to the degree θ. Preferably, the degree of hue change is smooth and changes as θ changes, as exemplified in FIG. 14B. In FIG. 13C, the user 1300 exhibits compensatory movement at or beyond a maximum threshold. On the display 1306, the avatar shadow 1308 correspondingly reaches a maximum change in hue. In some preferred embodiments, the target 1302 also becomes blocked so that the user is not allowed to obtain the goal of reaching even if actually reaching it. In some preferred embodiments, the successfully reaching the target will not result in completion of the activity and no indication that the target is reached or the goal of the game is reached is provided to the user.

During testing, the inventors discovered that tracking the trunk flexion for very high trunk flexion values is not guaranteed. This is probably because during high trunk flexion, in some embodiments, the tracking camera cannot properly track the base of the trunk as it is hidden by the upper flexing trunk. This causes the base of the trunk to be estimated, and it is estimated by aligning it to the top of the trunk. This causes the flexion value to be tracked as if the body was straight and not flexed. Because of this, the inventors found that measuring the trunk displacement so that when the trunk flexion suddenly decreases but the displacement continues to increase, it is preferable to still provide compensation feedback. For instances in which trunk flexion is tracked, it is preferable that the lower trunk position is saved as the last maximum trunk flexion tracked, and then the flexion used for feedback is calculated from this saved position.

Figure 15:
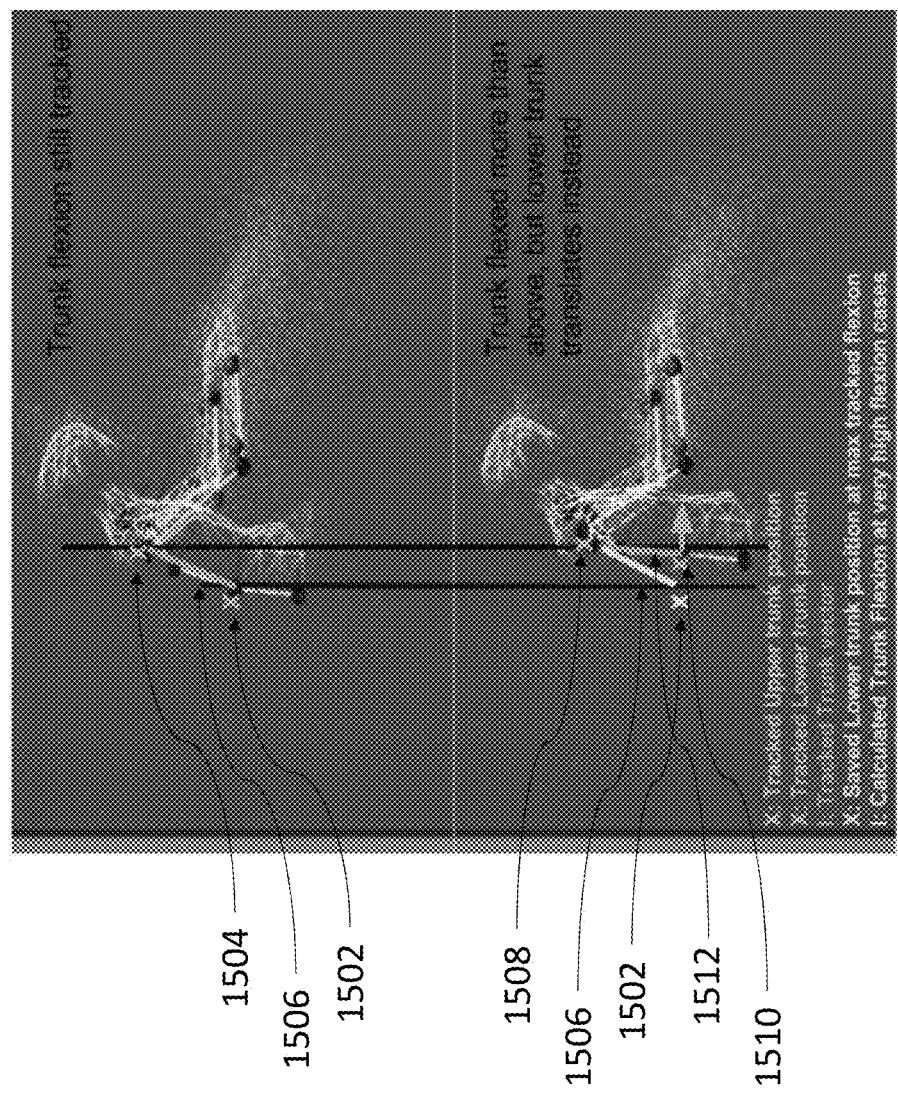
FIG. 15 illustrates a visual depiction of a body model during motion tracking with forward trunk flexion in accordance with embodiments.

Referring to FIG. 15, an exemplary visual of motion tracking with forward trunk flexion components identified is illustrated where flexion decreases but displacement continues. In the top portion of the figure, the base of the trunk position 1502 is tracked at a first position (not necessarily an initial, resting position) and the upper trunk portion position 1504 is tracked to create a forward flexion vector 1506. In the bottom portion of the figure, the trunk is flexed more than in the top portion of the figure, as evidenced by the upper trunk position 1508. As a result, the body may be considered to have moved forward in the tracking as evidenced by the different tracked lower trunk position 1510 and a different vector 1512. In preferred embodiments, compensation feedback is still provided in spite of the tracking resulting in a smaller or even 0 degree of flexion. In such cases, the lower trunk position 1502 is used rather than lower trunk position 1510 in determining flexion for determining compensation feedback.

Feedback for Single Joint Exercises/Activities

The single joint activity should enforce the usage of the wrist rotation. Wrist rotation refers to the change of hand orientation versus forearm orientation. Any other movement than wrist rotation is perceived as a compensatory movement. More specifically, this includes (a) displacement of the wrist (due to elbow, shoulder or trunk movement); (b) displacement of the elbow (due to shoulder or trunk movement). A tolerance threshold is allowed for each movement.

Figure 16B:
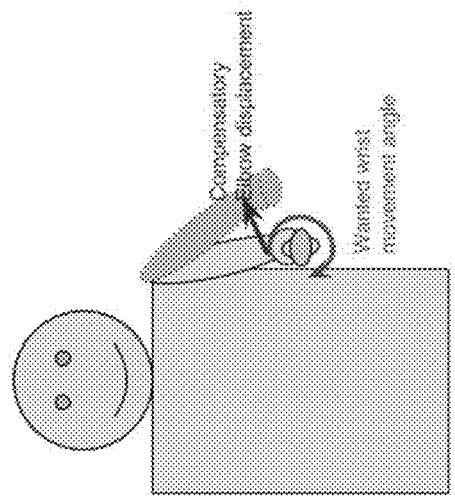
FIG. 16A-16C illustrate exemplary depictions of single joint compensation movements in accordance with embodiments.
Figure 16C:
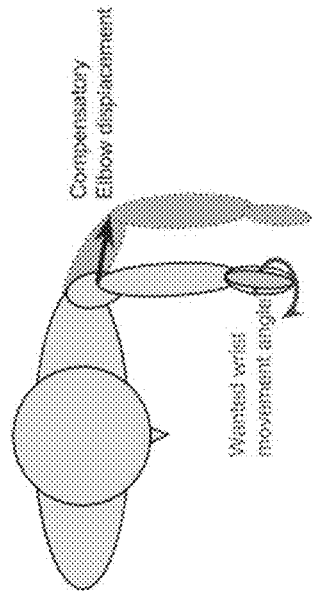
Figure 16A:
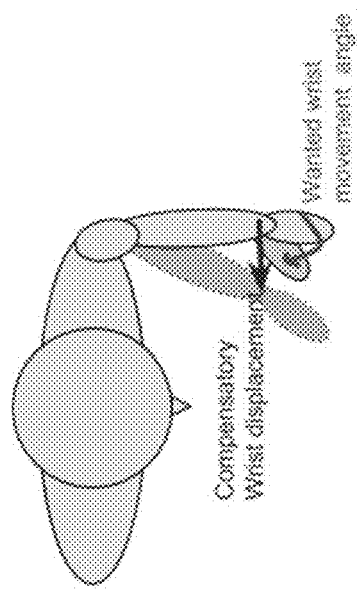

Referring now to FIGS. 16A-16C, illustrations of single joint compensation are shown. In FIG. 16A, wrist flexion/extension and/or radial/ulnar deviation movements are illustrated. In accordance with preferred embodiments, up to 3 cm displacement of the wrist is allowed from the start of trial wrist position. Blocking feedback is provided from a wrist displacement of 10 cm. Up to 3 cm displacement of the elbow is allowed from the start of trial elbow position. Blocking feedback is provided from an elbow displacement of 10 cm. In FIGS. 16B and 16C, pronation/supination movements are illustrated. In accordance with preferred embodiments, up to 3 cm displacement of the elbow is allowed from the start of trial angle and blocking feedback is provided from an elbow displacement of 10 cm.

TABLE 4

Feedback Thresholds (cm)

| Compensation Type | Start of Feedback Threshold | Maximum Feedback Threshold |
|---|---|---|
| Elbow displacement | 3 cm | 10 cm |
| Wrist displacement | 3 cm | 10 cm |

For this activity tracking directly the wrist and elbow markers are sufficient to detect compensatory movements. Because of this the marker positions can be tracked directly as opposed to using the hybrid tracking values of the wrist and elbows. If a marker can no longer be seen by the camera, for example if the user rotates his/her forearm so that the palm is facing up, the last tracked position will be used until the marker is seen by the camera again.

In some preferred embodiments, the compensatory threshold values can be adjusted either manually or automatically. For example, in some cases, values can be received from user input. In some cases, threshold values can be calibrated according to the patient. For example, a patient can exhibit less trunk flexion or other compensatory movement over the course of therapy and the threshold levels can be adjusted to allow less or more compensation as the patient advances. Thus, data representing the performance of a patient in activities and the amount of compensation (e.g., degree of trunk flexion, degree of elbow displacement, and the like) during activities can be used to determine threshold levels.

It should be understood that the compensatory movement feedback is integrated with the activity or exercise such that the user need not move attention away from the activity or exercise to receive it. Thus, feedback is incorporated into the elements of the activity that otherwise enhance the reality of the virtual reality environment. For example, as discussed above, feedback can be incorporated into a shadow of an avatar, the shadow included for rendering the avatar more realistic. Thus feedback is provided visually absent an element specifically dedicated to providing feedback or audially absent an audio element specifically dedicated to providing feedback and the like. It is possible in some embodiments to provide such integrated feedback in combination with a different type of feedback that is not integrated (e.g., integrated visual feedback and non-integrated audio feedback).

In some preferred embodiments, upper body compensation feedback can include other types of compensatory movements, including lateral trunk displacement, trunk axial rotation, shoulder elevation (i.e., shrugging). Skilled artisans can appreciate that the particular types of compensation that are measured and are provided feedback for can depend on the particular activity or exercise.

Figure 17A:
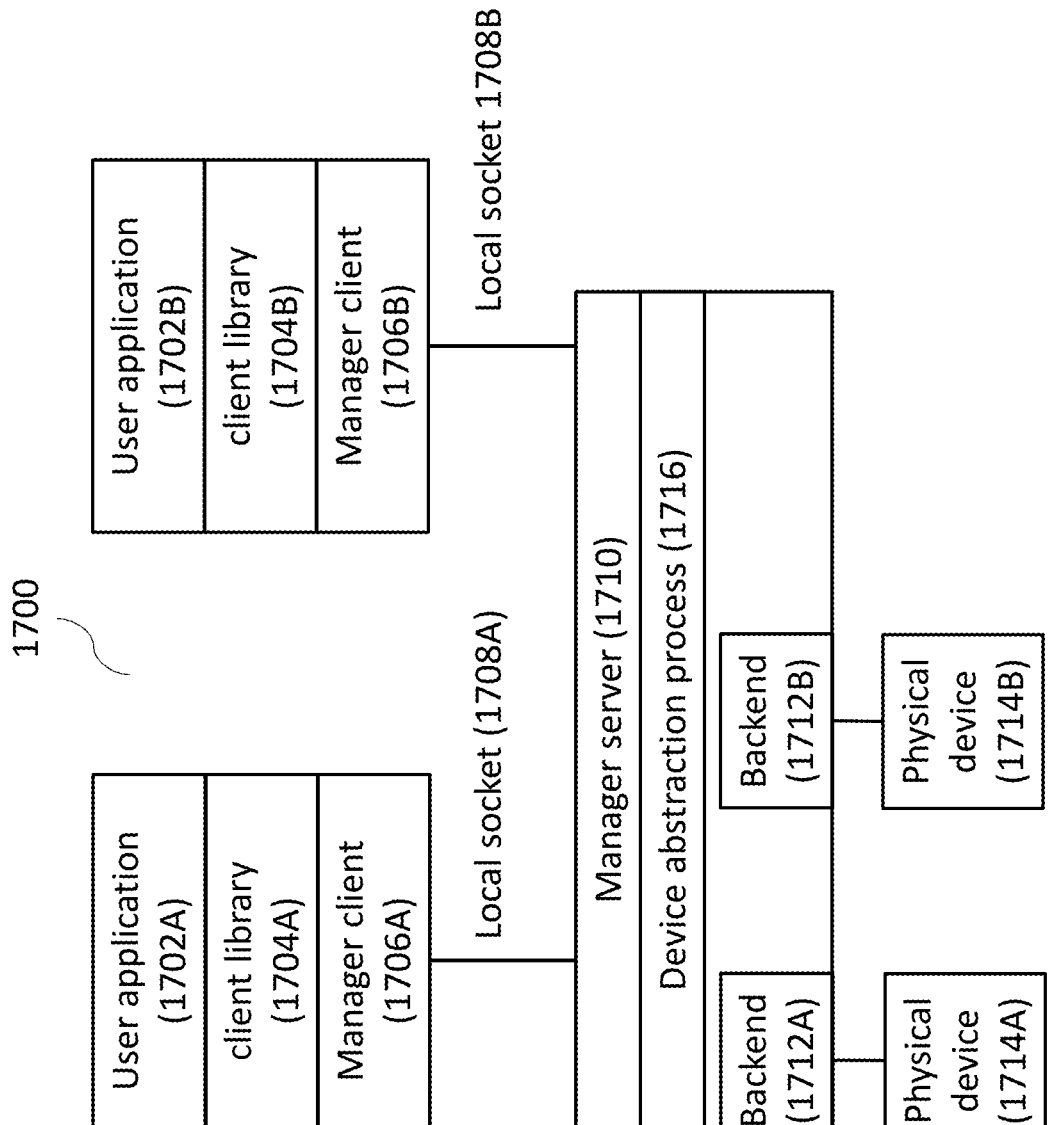

FIG. 17A shows an exemplary, non-limiting, illustrative system that incorporates a device abstraction layer, such as for example and without limitation device abstraction layer 108 of FIG. 1A.

As shown, a device abstraction system 1700 features a plurality of user applications 1702A and 1702B, communicating with a manager server 1710 through a local socket 1708A or 1708B, respectively. Each user application 1702 is assumed to be operated by a computational device (not shown for simplicity). Each of user applications 1702A and 1702B is in communication with a client library 1704A or 1704B, respectively, and a manager client 1706A or 1706B, respectively.

Manager server 1710 features a plurality of backends 1712A and 1712B, each of which is in communication with a physical device 1714A or 1714B. Manager server 1710 also operates a device abstraction process 1716, which receives data from physical devices 1714 through their respective backends 1712. Device abstraction process 1716 then communicates this data in a standardized manner to the appropriate manager client(s) 1706, which in turn pass the data to user application(s) 1702. User application(s) 1702 are able to consume abstracted data, such that they do not need to be aware of the specific features or functions of each physical device 1714, through client library 1704, which may be implemented as a shared instance of such a library. Preferably user applications 1702 receive the data through a shared memory, which may for example be implemented as described with regard to FIG. 17B.

Figure 17B:
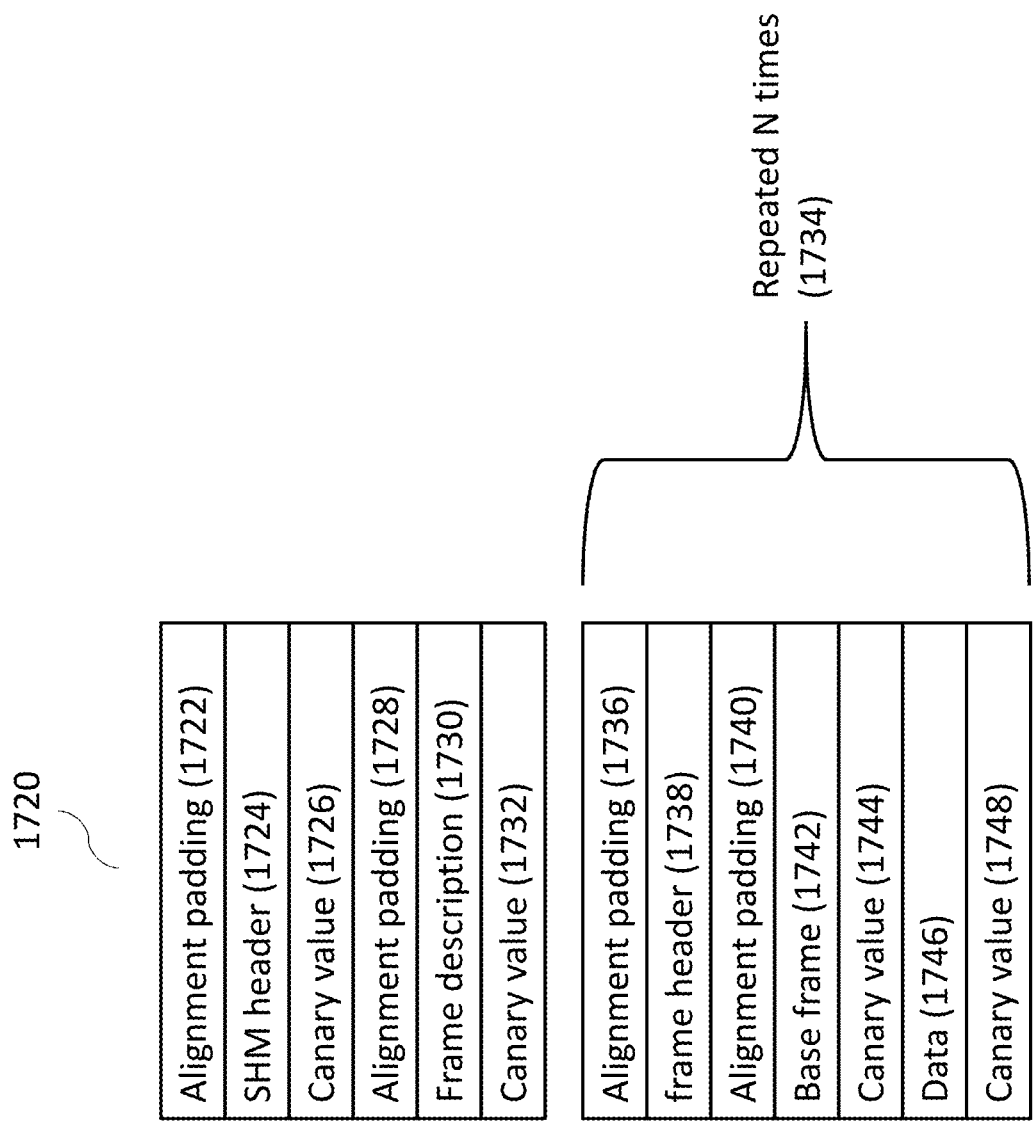
FIG. 17B shows an exemplary, non-limiting, illustrative shared memory buffer.

FIG. 17B shows an exemplary, non-limiting, illustrative shared memory buffer. In an embodiment of the system of the present invention, the system uses shared memory architecture where the provider (running in a server process in the system) writes data to a shared memory buffer that the client (running in the user process) can access. This is a single-producer, multiple consumers model.

To do this, each capability provider will allocate the following: a shared memory segment; a shared memory mutex; a shared memory condition variable. The mutex and condition variable are used to allow a consumer to wait for the next frame.

An example of such a layout is given in FIG. 17B. As shown, various items are shared through the shared memory segment 1720, including the frame descriptor (e.g. decaf_monorgb_frame_desc) 1730, a base frame 1742 and data 1746.

To maintain alignment, the layout includes alignment padding regions 1722, 1728, 1736, 1740. Canary values 1726, 1732, 1744 and 1748 are used for buffer overflow protection.

FIG. 18 shows an exemplary, non-limiting, illustrative data type description. As shown, a data type description 1800 features a plurality of layers, shown as three layers, for describing capabilities. A capability description 1802 features two tiers, a capability class 1804 and a capability format 1806. The top tier (Capability class) describes the broad category of the data—that is, from which type or category or sensor the data has been obtained. Example capability classes are "Image", "Range", "IMU" (inertial motion unit), "BioSig" (biosignals).

The second tier (Capability format) describes the format of the data. For image data, for example, this corresponds to the pixel format, e.g., "24 bit BGR", "RGBA32" and so forth.

The two top tiers form the capability for capability description 1802. It is what client software would request when querying for a capability.

The lowest tier (Description 1808) describes additional details about the data. An example description for "24 bit BGR" images is "1080×720 with 3240 stride". All tiers taken together form a full description of the data format which allows unambiguous interpretation of a data buffer.

Figure 19:
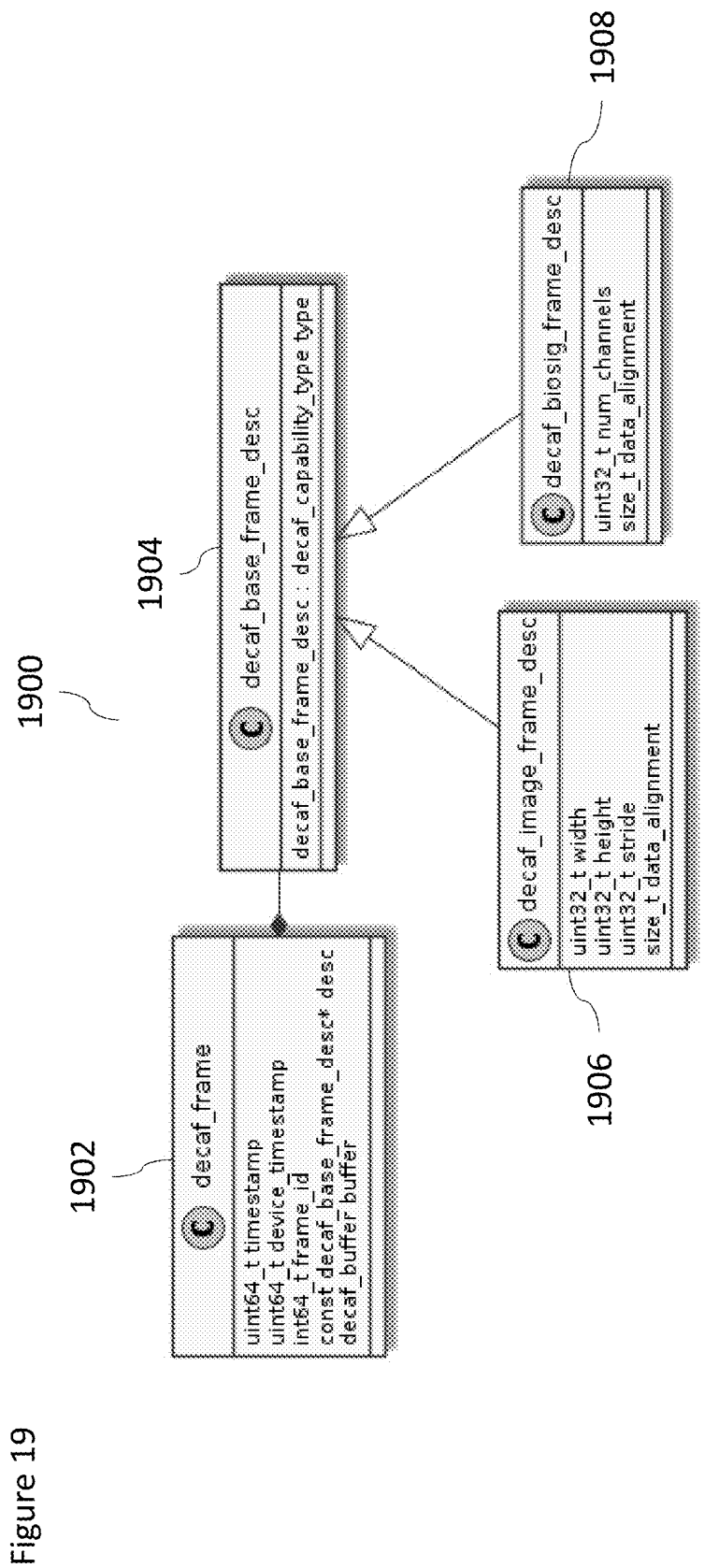
FIG. 19 shows an exemplary, non-limiting, illustrative frame class description.

FIG. 19 shows an exemplary, non-limiting, illustrative frame class description. A frame class description 1900 features an overall frame 1902 that includes pointers to the lowest tier information (description 1808) from FIG. 18 and to the actual data. Each instance of the data and of the description is provided through a base frame 1904. Helpers, such as an image frame describer 1906 and a biosig frame describer 1908, are provided to assist in interpreting the data.

Figure 20:
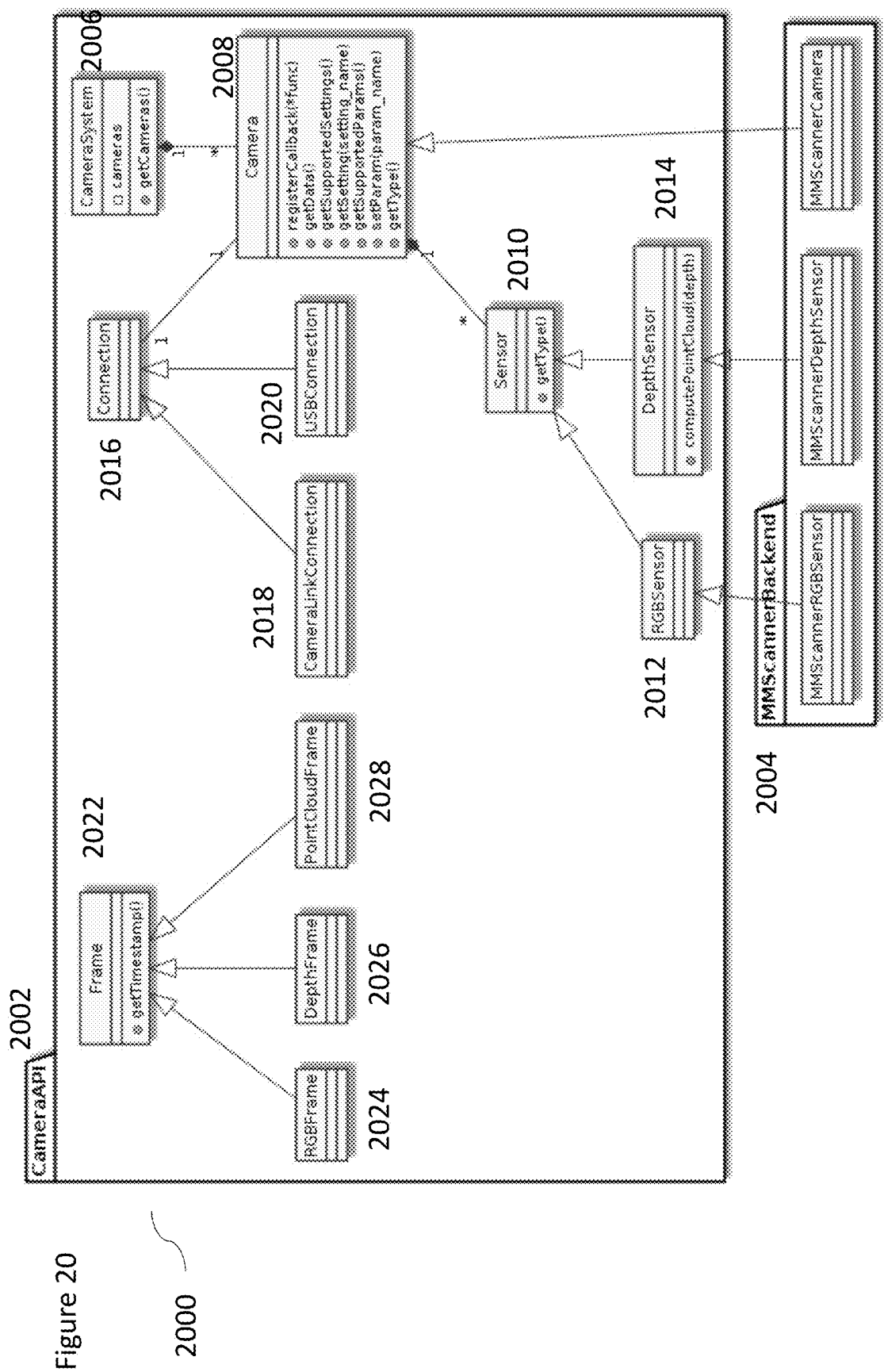
FIG. 20 shows an exemplary, non-limiting, illustrative camera API (application programming interface) abstraction.

FIG. 20 shows an exemplary, non-limiting, illustrative API (application programming interface) abstraction. An API abstraction 2000 features a camera API 2002 and a sensor back-end 2004. Camera API 2002 features a CameraSystem abstraction 2006. CameraSystem 2006 loads dynamically (at running time) a list of pre-compiled back-ends (dynamic libraries). This architecture generalizes the interface to support any arbitrary type hardware sensor. For example in FIG. 20, the MMScanner back-end implements support for an RGBD (Color+Depth) camera. However other back-ends could provide support for inertial sensors, EEG, or any other type of acquisition device that generates a data stream.

In this example, a camera is an abstraction that contains several sensors, such that Camera objects 2008 may for example connect through a sensor class 2010, which may for example feature an RGB sensor abstraction 2012 or a depth sensor abstraction 2014.

Abstraction 2016 is an abstraction of the connection bus with the hardware device. Abstraction 2016 makes the API agnostic to the physical connection of the device (Sensor) with the host. The non-limiting example shows the USB and CameraLink connections, but the generalization could apply to any type of physical connection or communications protocol (Ethernet, FireWire, BlueTooth, WiFi, etc. . . . ). In this example, abstraction 2016 connects to various specific connectors, such as a camera link connector 2018 and/or a USB connector 2020 for example.

The abstraction 2022 represents another generalization of the different data types provided by the back-ends. In the example, data types, including but not limited to one or more of RGB data 2024, depth data 2026 or point cloud data 2028, may be provided by a Camera back-end with Color and Depth sensors.

Camera objects 2008 instantiate the corresponding Frame (2022) data types depending on which back-end has been dynamically loaded. So for instance if the MMScannerBackend is dynamically loaded (in this example, loading data from an RGBD (red, green, blue, depth) camera device), the back-end modules will expose to the Camera module which type of data the device is able to provide. The Camera (2008) will then generate the corresponding data types and expose them to the API user. This datatype-agnostic strategy is also used with other parameters that are specific for the configuration of the device, such as the frequency, light-exposure, internal inclinometer sensors, calibration parameters, and so forth, so that the usability of the hardware is not limited by the generalization ability of the API.

Optionally, in each iteration of the camera loop, the camera checks if there's data in the device, asks each sensor for a free buffer, fills it, asks the sensor to process it, and pushes it back into the sensor "processed" buffer ring (and if callbacks registered calls them).

The operation of pushing back is done atomically for all the sensors of a camera (this means that all cameras pushed a processed buffer at once) with a shared mutex.

When the buffer pool is empty, new data coming from a connection is skipped. The buffer ring with processed data should be released after used by the client and brought back to the free buffer pool, or should be automatically released after certain time.

The back-end code should only implement the Camera initialization (adding its sensors), a virtual method in the camera that transforms raw data from the device into Frames, and virtual methods in the sensors that perform the processing of Frames. A client can at any time ask a Camera (or a sensor) for its most recent data (pops a processed frame from the buffer ring)

Figure 21:
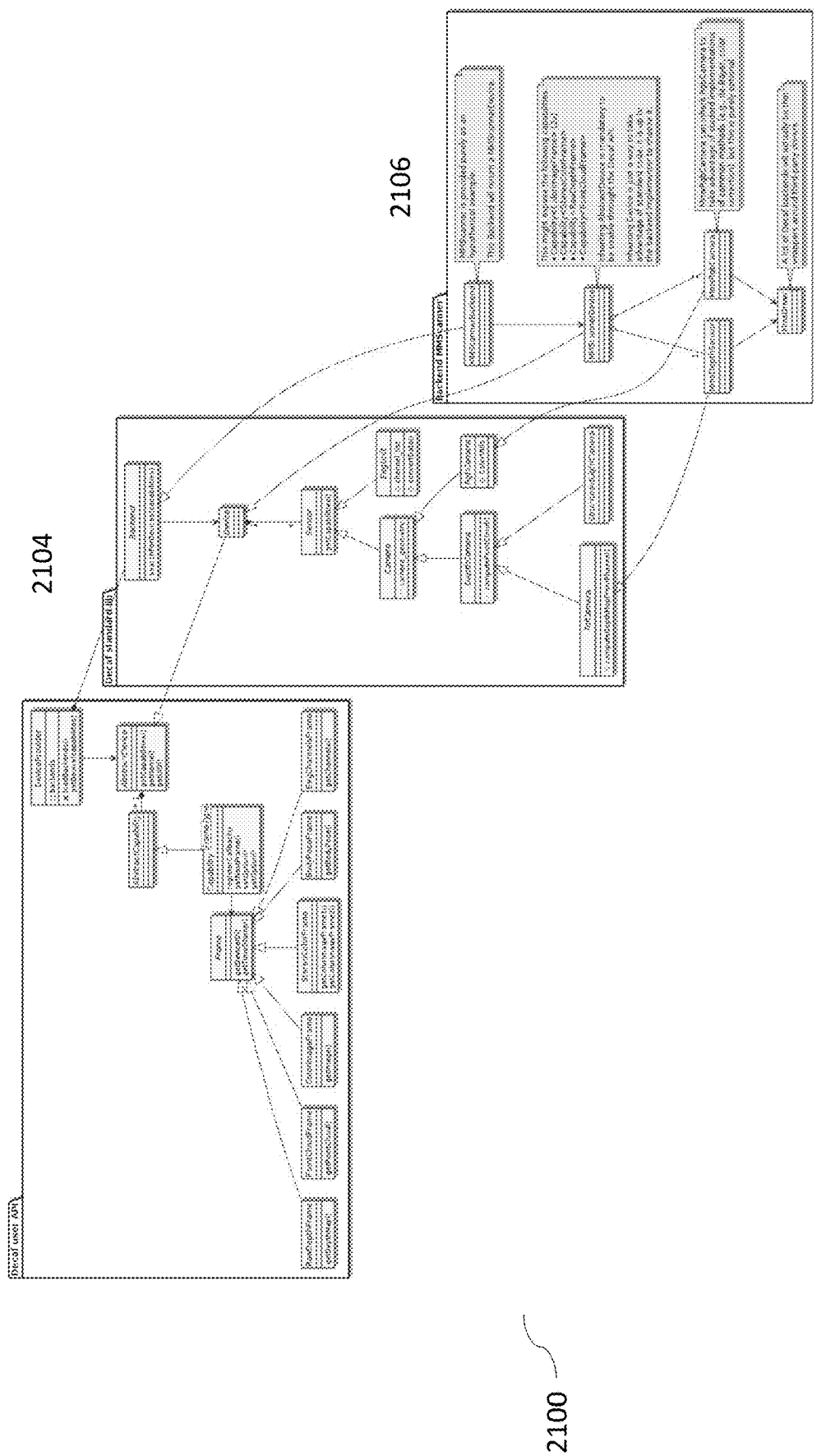
FIG. 21 shows an exemplary, non-limiting Unified Modeling Language (UML) diagram of the components of the API from the system to the backend.

FIG. 21 shows an exemplary, non-limiting Unified Modeling Language (UML) diagram of the components of the API from the system to the backend, as a flow 2100. Flow 2100 moves between a user API 2102, which exposes capabilities of the device abstraction layer to a user application; a standard client library 2104 for the device abstraction layer and a backend 2106 for a particular device, which in this non-limiting example is called "MMScanner".

A device is a software representation of a logical input device. It can provide several types of data, by exposing capabilities. A device will often correspond to a physical device, but this does not have to be the case. Multiple physical devices may be combined or otherwise abstracted. For example, to create a new device that represents multiple physical devices, one would then write a new "composition" backend, providing a device that wraps the drivers to the multiple devices and provides the relevant capabilities.

A device is preferably defined in terms of its capabilities. Various non-limiting examples are as follows; mmscanner camera (provides RGB, RGB stereo and depth); kinect (provides bodypose+pointcloud); Colibri inertial sensors (provides data from N inertial sensors); EEG acquisition device (provides eeg channels).

A Capability represents the capability of a device to provide certain types of data. The data itself will be represented by a sequence of Frame objects, either queried directly through a getNextFrame( ) method, or by means registering a callback function. Capabilities do not necessarily match exactly the sensors of a device. Take for example a depth camera; it might expose a RawDepth and a PointCloud capabilities that rely on data from the same sensor but provide it in different forms.

In order for the user application to be able to receive the data, capabilities preferably communicate in terms of frame types. Data is communicated according to frames, so that the data type and format is clear. Each frame includes a device ID and a timestamp. Non-limiting examples of data types include RawDepthFrame, PointCloudFrame, colorImageFrame, StereoColorFrame, BodyPoseFrame, and EEGChannelsFrame.

Capabilities exposed by a single device are assumed to be synchronized, i.e., the Frame timestamps are assumed to be coherent among the different Frame objects returned by the Capabilities of a single device. A user is of course free to use several devices (and thus extend the range of Capabilities), but the timestamps might not be coherent in that case and synchronization is up to the user. Non-limiting examples of capabilities include: ColorImage; StereoColorImages; RawDepthMap; PointCloud; BodyPose; InertialSensorOrientation; InertialSensorAcceleration; EEGChannels.

As shown with regard to user API 2102, a DeviceProvider provides the entry point into client library 2104 for clients (client applications). The client asks the DeviceProvider for available devices that match a set of required capabilities. Underneath, the DeviceProvider loads all the available backends (preferably dynamically), and asks each backend (such as backend 2106) whether it supports the relevant capabilities and, if it is the case, asks for the devices it can find currently.

The backends are responsible for returning AbstractDevice instances for consumption by Decaf end users. Their only obligation is to provide a Backend instance that can be dynamically loaded by the DeviceProvider and by correctly inheriting AbstractDevice to provide Capabilities.

User API 2102 interacts with an abstracted device, in order to obtain the data required according to the requested capabilities of the device. Client library 2104 provides the data according to the abstracted device model, such that user API 2102 does not need to implement details of any device drivers or other device specific features. Client library 2104 receives the data from the backend of the device, such as backend 2106, which does include any wrappers for device drivers and other device-specific features.

Optionally, various sensor types and data sources are used to obtain the necessary data for further analysis as described above. Table 5 shows a non-limiting list of such devices, the capabilities of each device (according to the data that can be provided), the raw data format and some exemplary user formats.

TABLE 5

Devices and Resultant Data

| Device | Capabilities (several per device) | Raw data | Typical user formats |
| --- | --- | --- | --- |
| Depth camera | Depth map | Amplitude image Phase image | Depth image Point Cloud |
| Kinect2 | Color, Depth map | IR Image (amplitude) Depth map Color image | Depth image Point Cloud Color |
| Camera such as Simple Webcam | Color | Color image (BGR) | Color |
| Lyra | Depth map, Color, IMU | Amplitude image Phase image Color image IMU | Depth image Point Cloud Color IMU |
| Elvira | Depth map, Color, IMU, Biosignals | Phases, Bayered stereo, IMU int24 biosignal data | Depth image Point Cloud Color IMU int24 or scaled float biosignal data |
| Mindleap | IMU, Biosignals | IMU int24 biosignal data | IMU int24 or scaled float biosignals data |

SimpleWebcam is a backend made with OpenCV that retrieves the first available standard camera on a local computer.

The LYRA device is described for example in U.S. patent application Ser. No. 15/891,235, filed on 7 Feb. 2018, owned in common with the present application and hereby set forth as if fully incorporated herein. The ELVIRA device is described for example in U.S. patent application Ser. No. 15/555,561, filed on 5 Sep. 2017, owned in common with the present application and hereby set forth as if fully incorporated herein.

Figure 22:
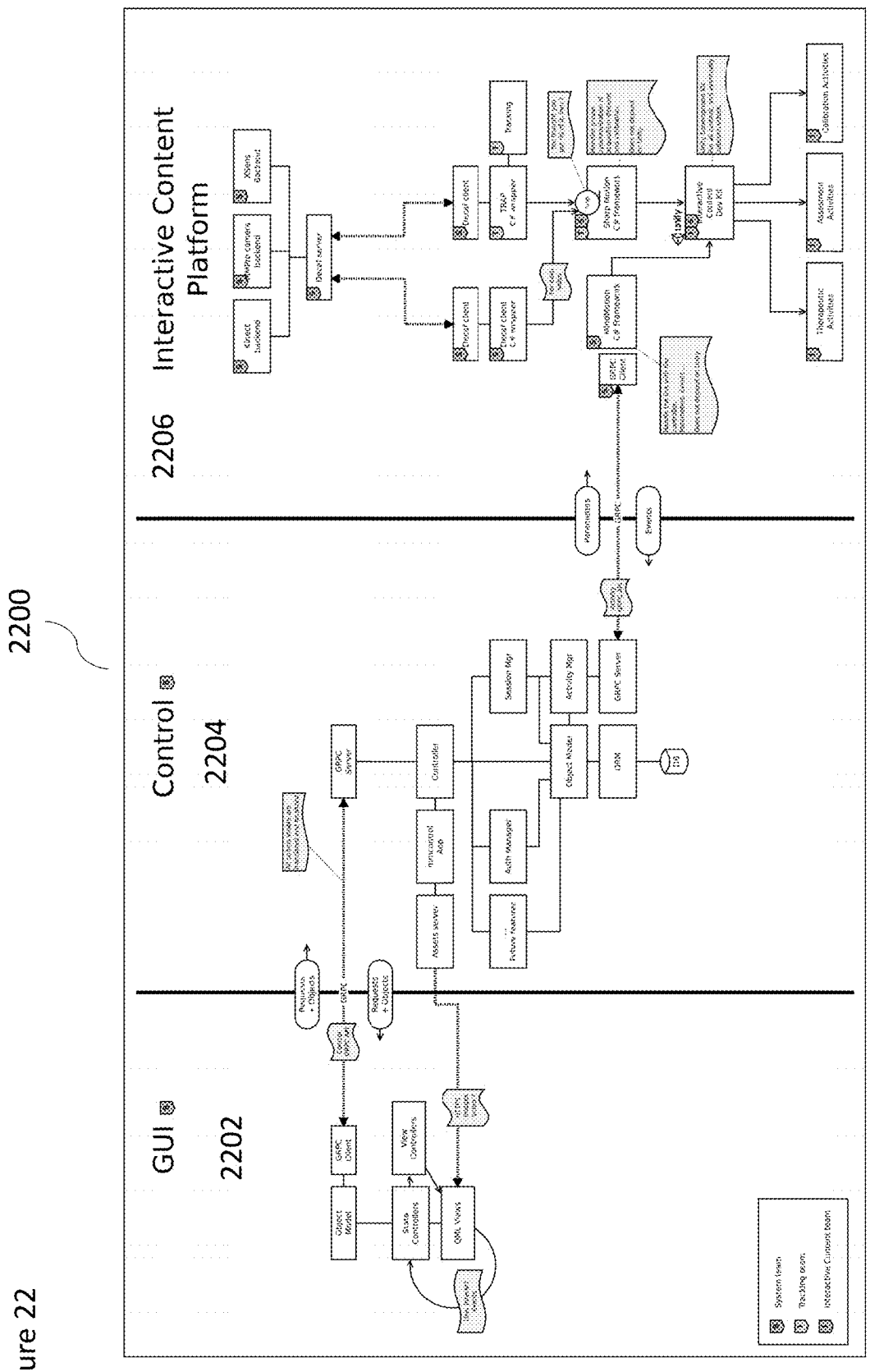
FIG. 22 shows an exemplary, non-limiting, illustrative system according to at least some embodiments.

FIG. 22 shows an exemplary, non-limiting, illustrative system according to at least some embodiments. As shown a system 2200 features a GUI 2202, a control 2204 and an interactive content platform 2206. Interactive content platform 2206 serves one or more games, handles device abstraction and provides data. The previously described device backends, client libraries, etc. of FIGS. 17-21 may optionally be implemented at interactive content platform 2206. Optionally, interactive content platform 2206 also provides various reports and analyses of activities, including but not limited to activities provided with regard to therapeutic activities, calibration activities and assessment activities.

Control 2204 supports interactive content platform 2206, by passing parameters to interactive content platform 2206 (from GUI 2202) and receiving events from interactive content platform 2206 (which are then sent to GUI 2202). Optionally, transmission of information across system 2200 is performed according to a remote object protocol, such as GRPC (Google remote procedure call) for example.

Control 2204 may include two servers for the remote protocol, shown as two GRPC servers, for supporting remote object protocol communication with each of interactive content platform 2206 and GUI 2202. The games are managed through control 2204, through an activity manager and a session manager. Each session preferably includes a plurality of games and/or activities, so the session manager manages the overall session.

Control 2204 also preferably includes an object model, which is a data model. This data model is able to receive (load) data from the database, manipulate it and push the data back to the database. The data model includes information necessary for operation of system 2200, including but not limited to data about the patient and therapist; credentials, parameters, type of illness, other necessary definitions and so forth. GUI 2202 also includes an object model, which it uses to exchange objects, to display data and to receive commands; as well as state controllers and view controllers.

Figure 23:
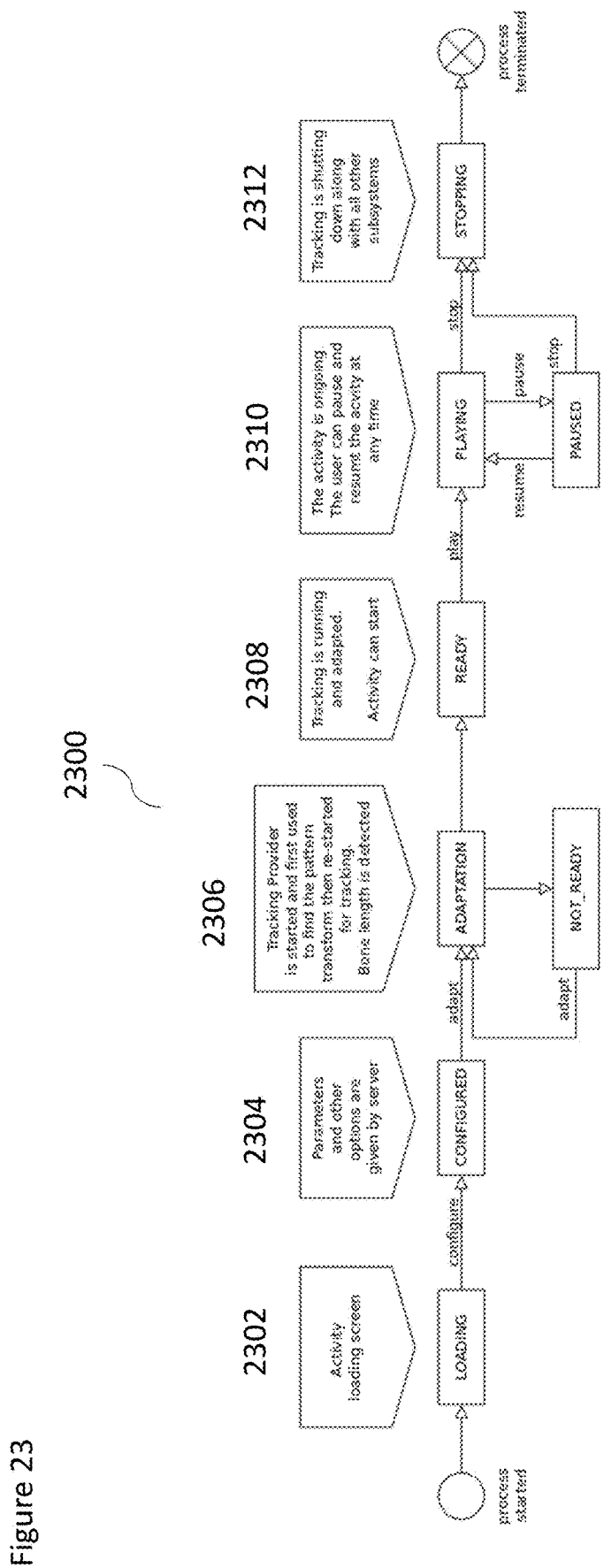
FIG. 23 shows an exemplary, non-limiting, illustrative flow.

FIG. 23 shows an exemplary, non-limiting, illustrative flow for operating the exemplary system of FIG. 22. As shown in a flow 2300, the process begins with loading an activity into the system in 2302. Next parameters and other options are provided from the control to the interactive game platform, in 2304. Tracking calibration is performed and tracking begins in 2306; this stage may repeat until tracking has been established. Tracking is performed through the interactive game platform; the control may indicate to the user or therapist, through the GUI, whether further calibration is required.

In 2308, the system indicates that it is ready for gameplay to begin, after tracking has been adapted and is ready. A message to this effect may be displayed through the GUI. During gameplay in 2310, the activity may be paused through the GUI by the user or the therapist, and may then be restarted. Once the command to stop has been provided through the GUI in 2312, tracking and other processes shut down, and gameplay stops.

Any and all references to publications or other documents, including but not limited to, patents, patent applications, articles, webpages, books, etc., presented in the present application, are herein incorporated by reference in their entirety.

Example embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements from any other disclosed methods, systems, and devices, including any and all elements corresponding to systems, methods and apparatuses/device for tracking a body or portions thereof. In other words, elements from one or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure). Correspondingly, some embodiments of the present disclosure may be patentably distinct from one and/or another reference by specifically lacking one or more elements/features. In other words, claims to certain embodiments may contain negative limitation to specifically exclude one or more elements/features resulting in embodiments which are patentably distinct from the prior art which include such features/elements.

What is claimed is:

1. A system for performing rehabilitation or training of a subject, comprising:
    a depth sensor for providing data to determine the three dimensional location of the body in space according to the distance from depth sensor;
    a body model;
    a computational device having computer instructions operating thereon configured to analyze said data from said depth sensor according to said body model, to detect a compensation movement of a body part having a displacement angle from a neutral axis that is greater than a first threshold angle, to adjust the appearance of an existing display element according to a gradient, the gradient corresponding to the degree of compensation beyond the first threshold angle, and if the degree of compensation is greater than a second threshold angle, changing the appearance of the existing display element to a maximum state;
    a display for displaying the display element and information to the subject according to said analyzed data; and
    a frame for holding said computational device and said display;
    wherein said body part comprises a trunk, a shoulder or a combination thereof; said compensation movement comprises trunk forward displacement, trunk lateral displacement, trunk rotation, shoulder elevation, shoulder abduction, elbow flexion or a combination thereof; said compensation movement occurs during movement of a hand; said compensation movement causes said body part to be displaced out of a plane of movement wherein such compensation is not performed; and the body part is the trunk of the user and the first threshold angle is 7 degrees and the second threshold angle is 20 degrees.

2. The system of claim 1, adapted for being mobile.

3. The system of claim 2, adapted for a subject who is seated.

4. The system of claim 2, adapted for a subject who is reclining.

5. The system of claim 1, wherein said depth sensor is attached to said frame.

6. The system of claim 1, wherein said depth sensor is attached to said display.

7. The system of claim 1, further comprising a controller for controlling at least one function of said computational device.

8. The system of claim 7, wherein said controller is attached to said frame.

9. The system of claim 8, wherein said controller and said display are attached to a single pillar of said frame.

10. A method, comprising:
    detecting a compensation movement of a body part having a displacement angle from a neutral axis that is greater than a first threshold angle, said first threshold angle determined according to a range of motion defined according to a plurality of subjects who do not suffer from a neurological deficit;
    adjusting the appearance of an existing display element according to a gradient, the gradient corresponding to the degree of compensation beyond the first threshold angle; and
    if the degree of compensation is greater than a second threshold angle, changing the appearance of the existing display element to a maximum state;
    wherein the body part is the trunk of the user and the first threshold angle is 7 degrees and the second threshold angle is 20 degrees.

11. The method of claim 10, wherein the adjusting the appearance of an existing display element comprises changing the tone, shade, tint, or hue or changing the transparency of the display element and the maximum state comprises a color substantially free of tone, shade, or tint or substantially transparence.

12. The method of claim 10, wherein the adjusting the appearance of an existing display element comprises changing the tone, shade, tint, or hue or changing the transparency of the display element and the maximum state comprises a color substantially free of tone, shade, or tint or substantially transparence.

13. The method of claim 10, wherein said neurological deficit is caused by a condition selected from the group consisting of a stroke, a physical accident, a neurological disease or a combination thereof.

14. A method, comprising:
    detecting a compensation movement of a body part having a displacement distance from a resting position that is greater than a first threshold distance, said displacement distance measured during an activity of a single joint, wherein said body part having said displacement distance is different from said single joint;
    adjusting the appearance of an existing display element according to a gradient, the gradient corresponding to the compensation distance beyond the first threshold distance; and
    if the compensation distance is greater than a second threshold distance, changing the appearance of the existing display element to a maximum state;

wherein the body part is the trunk of the user and the first threshold angle is 7 degrees and the second threshold angle is 20 degrees.

15. A system for performing rehabilitation or training of a subject, comprising:
   a depth sensor for providing data to determine the three dimensional location of the body in space according to the distance from the depth sensor;
   a body model;
   a computational device having computer instructions operating thereon configured to analyze said data from said depth sensor according to said body model, to detect a compensation movement of a body part having a displacement angle from a neutral axis that is greater than a first threshold angle, to adjust the appearance of an existing display element according to a gradient, the gradient corresponding to the degree of compensation beyond the first threshold angle, and if the degree of compensation is greater than a second threshold angle, changing the appearance of the existing display element to a maximum state;
   a display for displaying the display element and information to the subject according to said analyzed data; and
   a frame for holding said computational device and said display;
   wherein said body part comprises a trunk, a shoulder or a combination thereof; said compensation movement comprises trunk forward displacement, trunk lateral displacement, trunk rotation, shoulder elevation, shoulder abduction, elbow flexion or a combination thereof; said compensation movement occurs during movement of a hand; said compensation movement causes said body part to be displaced out of a plane of movement wherein such compensation is not performed; said body part comprises said trunk and said trunk is determined to be participating in a compensatory movement if said first threshold is greater than 7 degrees.

16. A method, comprising:
   detecting a compensation movement of a body part having a displacement angle from a neutral axis that is greater than a first threshold angle;
   adjusting the appearance of an existing display element according to a gradient, the gradient corresponding to the degree of compensation beyond the first threshold angle;
   if the degree of compensation is greater than a second threshold angle, changing the appearance of the existing display element to a maximum state; wherein said body part comprises a trunk and wherein said trunk is determined to participate in said compensation movement if said first threshold angle is greater than 7 degrees.

17. A method, comprising:
   detecting a compensation movement of a body part having a displacement distance from a resting position that is greater than a first threshold distance, said displacement distance is measured during an activity of a single joint, said single joint does not comprise said body part having said displacement distance, such that said single joint is not part of said body part or vice versa;
   adjusting the appearance of an existing display element according to a gradient, the gradient corresponding to the compensation distance beyond the first threshold distance; and
   if the compensation distance is greater than a second threshold distance, changing the appearance of the existing display element to a maximum state;
   wherein the body part is the trunk of the user and the first threshold angle is 7 degrees and the second threshold angle is 20 degrees.

* * * * *